United States Patent
Yu et al.

(10) Patent No.: US 9,902,779 B2
(45) Date of Patent: Feb. 27, 2018

(54) ANTIBODIES, PHARMACEUTICAL COMPOSITIONS AND USES THEREOF

(71) Applicant: OBI PHARMA, INC., Taipei (TW)

(72) Inventors: Cheng-Der Tony Yu, Taipei (TW); Jiann-Shiun Lai, Taipei (TW); I-Ju Chen, Taipei (TW); Cheng-Chi Wang, Taipei (TW); Yi-Chien Tsai, Taipei (TW)

(73) Assignee: OBI PHARMA INC., Taipei (TW)

( * ) Notice: Subject to any disclaimer, the term of this patent is extended or adjusted under 35 U.S.C. 154(b) by 0 days.

(21) Appl. No.: 15/303,132

(22) PCT Filed: Apr. 10, 2015

(86) PCT No.: PCT/US2015/025305
§ 371 (c)(1),
(2) Date: Oct. 10, 2016

(87) PCT Pub. No.: WO2015/157629
PCT Pub. Date: Oct. 15, 2015

(65) Prior Publication Data
US 2017/0029526 A1 Feb. 2, 2017

Related U.S. Application Data

(60) Provisional application No. 62/057,381, filed on Sep. 30, 2014, provisional application No. 61/977,824, filed on Apr. 10, 2014.

(51) Int. Cl.
| | |
|---|---|
| *A61K 39/395* | (2006.01) |
| *C07K 16/28* | (2006.01) |
| *C07K 16/30* | (2006.01) |
| *C07K 16/32* | (2006.01) |
| *G01N 33/574* | (2006.01) |
| *C12N 5/16* | (2006.01) |
| *C07K 16/44* | (2006.01) |
| *A61K 39/00* | (2006.01) |

(52) U.S. Cl.
CPC ............ *C07K 16/30* (2013.01); *C07K 16/303* (2013.01); *C07K 16/3015* (2013.01); *C07K 16/44* (2013.01); *C12N 5/163* (2013.01); *G01N 33/574* (2013.01); *A61K 2039/505* (2013.01); *C07K 2317/14* (2013.01); *C07K 2317/24* (2013.01); *C07K 2317/33* (2013.01); *C07K 2317/565* (2013.01); *C07K 2317/72* (2013.01); *C07K 2317/92* (2013.01); *G01N 2400/02* (2013.01); *G01N 2440/38* (2013.01)

(58) Field of Classification Search
CPC .... C07K 16/18; C07K 16/30; C07K 16/3007; C07K 16/308; C07K 16/3076; C07K 16/3084; C07K 16/46; C07K 16/461; C07K 16/464; C07K 16/465; C07K 2317/50; C07K 2317/515; C07K 2317/56; C07K 2317/565; A61K 39/395; A61K 39/39533; A61K 39/39558; A61K 39/39583

See application file for complete search history.

(56) References Cited

U.S. PATENT DOCUMENTS

| | | |
|---|---|---|
| 2006/0165695 A1 | 7/2006 | Shitara et al. |
| 2009/0317411 A1 | 12/2009 | Wong et al. |
| 2012/0177664 A1 | 7/2012 | Yokoseki et al. |
| 2013/0144034 A1 | 6/2013 | Van Peij et al. |
| 2013/0344089 A1 | 12/2013 | Sjoblom-Hallen et al. |

FOREIGN PATENT DOCUMENTS

| | | |
|---|---|---|
| TW | 201100098 | 1/2011 |
| WO | 9306213 A1 | 4/1993 |
| WO | 0171005 A2 | 9/2001 |
| WO | 2004005349 A2 | 1/2004 |
| WO | 2011136911 A2 | 11/2011 |
| WO | 2013052745 A1 | 4/2013 |
| WO | 2013126746 A2 | 8/2013 |
| WO | 2015109180 | 7/2015 |
| WO | 2015143123 | 9/2015 |
| WO | 2015157629 A2 | 10/2015 |

OTHER PUBLICATIONS

Almagro & Fransson, Frontiers in Bioscience 2008; 13:1619-33.*
Casset, Biochemical and Biophysical Research Communications, 2003, vol. 307, pp. 198-205.*
Violette, P.D., et al., J Am. Board Fam. Med., 25: 111-119, 2012.*
Kinsinger, L.S., et al, Ann Intern. Med. 137: 59-67, 2002.*
Hung J. et al, "A Monoclonal Anti-Globo H Antibody, VK9 can mediate CDC/ADCC and Inhibit Adhesion of Globo H+ Cancer Cells to Extracellular Matrix", Cancer Research, Apr. 2012, vol. 72. Issue 8.
Adobati E, et al, "In Vitro Mimicry of CaMBr1 Tumor-Associated Antigen by Synthetic Oligosaccharides", Glycobiology, Jan. 1997, vol. 7, Issue 2, pp. 173-178.
Cascinelli N, et al, "Evaluation of Toxic Effects Following Administration of Monoclonal Antibody MBr1 in Patients with Breast Cancer". PubMed, Jun. 1986, pp. 267-271.
Search Report and Written Opinion of the Intellectual Property Office of Singapore, Application No. 11201607258S, dated Sep. 5, 2017.
European Search Report and Written Opinion No. EP15777370, dated Sep. 8, 2017.
First Examination Report of New Zealand dated Oct. 6, 2017.

\* cited by examiner

*Primary Examiner* — Misook Yu
*Assistant Examiner* — Anne L Holleran
(74) *Attorney, Agent, or Firm* — Michael Ye; Andrews Kurth Kenyon LLP

(57) ABSTRACT

The present invention provides antibodies or the antigen-binding portion thereof, that bind to one or more carbohydrate antigens. Also disclosed herein are pharmaceutical pharmaceutical compositions and methods for the inhibition of cancer cells in a subject in need thereof. The pharmaceutical compositions comprise an antibody or an antigen-binding portion thereof and at least one pharmaceutically acceptable carrier.

11 Claims, 5 Drawing Sheets

SEQUENCE LISTING

<160> NUMBER OF SEQ ID NOS: 90

<210> SEQ ID NO 1
<211> LENGTH: 348
<212> TYPE: DNA
<213> ORGANISM: mouse

<400> SEQUENCE: 1

```
tctggccctg ggatattgca gccctcccag accctcagtc tgacttgttc tttctctgga      60
ttttcactgt acacttttga tatgggtgta ggctggattc gtcagccttc agggaagggt     120
ctggagtggc tggcacacat tggtgggat gatgataagt actataaccc agccctgaag      180
agtcggctca cagtctccaa ggatacctcc aaaaaccagg tcttcctcaa gatccccaat     240
gtggacactg cagatagtgc cacatactac tgtgctcgag taaggggcct ccatgattat     300
tactactggt ttgcttactg gggccaaggg actctggtca ctgtctct                  348
```

<210> SEQ ID NO 2
<211> LENGTH: 282
<212> TYPE: DNA
<213> ORGANISM: mouse

<400> SEQUENCE: 2

```
gcatctccag gggagaaggt cacaatgact tgcagggcca gttcaagtgt aagttacatg      60
cactggtacc agcagaagcc aggatcctcc cccaaaccct ggatttatgc cacatccaac     120
ctggcgtctg gagtccctgc tcgcttcagt ggcagtgggt ctgggacctc ttactctctc     180
acaatcagca gagtggaggc tgaagatgct gccacttatt tctgccagca gtggagtcga     240
aacccattca cgttcggctc ggggacaaag ttggaaataa ga                        282
```

<210> SEQ ID NO 3
<211> LENGTH: 116
<212> TYPE: PRT
<213> ORGANISM: mouse

<400> SEQUENCE: 3

```
Ser Gly Pro Gly Ile Leu Gln Pro Ser Gln Thr Leu Ser Leu Thr Cys
1               5                   10                  15

Ser Phe Ser Gly Phe Ser Leu Tyr Thr Phe Asp Met Gly Val Gly Trp
            20                  25                  30

Ile Arg Gln Pro Ser Gly Lys Gly Leu Glu Trp Leu Ala His Ile Trp
        35                  40                  45

Trp Asp Asp Asp Lys Tyr Tyr Asn Pro Ala Leu Lys Ser Arg Leu Thr
    50                  55                  60

Val Ser Lys Asp Thr Ser Lys Asn Gln Val Phe Leu Lys Ile Pro Asn
65                  70                  75                  80
```

```
Val Asp Thr Ala Asp Ser Ala Thr Tyr Tyr Cys Ala Arg Val Arg Gly
                85                  90                  95

Leu His Asp Tyr Tyr Tyr Trp Phe Ala Tyr Trp Gly Gln Gly Thr Leu
            100                 105                 110

Val Thr Val Ser
        115

<210> SEQ ID NO 4
<211> LENGTH: 94
<212> TYPE: PRT
<213> ORGANISM: mouse

<400> SEQUENCE: 4

Ala Ser Pro Gly Glu Lys Val Thr Met Thr Cys Arg Ala Ser Ser Ser
1               5                   10                  15

Val Ser Tyr Met His Trp Tyr Gln Gln Lys Pro Gly Ser Ser Pro Lys
            20                  25                  30

Pro Trp Ile Tyr Ala Thr Ser Asn Leu Ala Ser Gly Val Pro Ala Arg
        35                  40                  45

Phe Ser Gly Ser Gly Ser Gly Thr Ser Tyr Ser Leu Thr Ile Ser Arg
    50                  55                  60

Val Glu Ala Glu Asp Ala Ala Thr Tyr Phe Cys Gln Gln Trp Ser Arg
65                  70                  75                  80

Asn Pro Phe Thr Phe Gly Ser Gly Thr Lys Leu Glu Ile Arg
                85                  90

<210> SEQ ID NO 5
<211> LENGTH: 8
<212> TYPE: PRT
<213> ORGANISM: mouse

<400> SEQUENCE: 5

Tyr Thr Phe Asp Met Gly Val Gly
1               5

<210> SEQ ID NO 6
<211> LENGTH: 16
<212> TYPE: PRT
<213> ORGANISM: mouse

<400> SEQUENCE: 6

His Ile Trp Trp Asp Asp Lys Tyr Tyr Asn Pro Ala Leu Lys Ser
1               5                   10                  15

<210> SEQ ID NO 7
<211> LENGTH: 13
<212> TYPE: PRT
<213> ORGANISM: mouse

<400> SEQUENCE: 7

Val Arg Gly Leu His Asp Tyr Tyr Tyr Trp Phe Ala Tyr
1               5                   10

<210> SEQ ID NO 8
<211> LENGTH: 10
<212> TYPE: PRT
<213> ORGANISM: mouse

<400> SEQUENCE: 8

Arg Ala Ser Ser Ser Val Ser Tyr Met His
1               5                   10
```

```
<210> SEQ ID NO 9
<211> LENGTH: 7
<212> TYPE: PRT
<213> ORGANISM: mouse

<400> SEQUENCE: 9

Ala Thr Ser Asn Leu Ala Ser
1               5

<210> SEQ ID NO 10
<211> LENGTH: 9
<212> TYPE: PRT
<213> ORGANISM: mouse

<400> SEQUENCE: 10

Gln Gln Trp Ser Arg Asn Pro Phe Thr
1               5

<210> SEQ ID NO 11
<211> LENGTH: 14
<212> TYPE: PRT
<213> ORGANISM: mouse

<400> SEQUENCE: 11

Trp Ile Arg Gln Pro Ser Gly Lys Gly Leu Glu Trp Leu Ala
1               5                   10

<210> SEQ ID NO 12
<211> LENGTH: 15
<212> TYPE: PRT
<213> ORGANISM: mouse

<400> SEQUENCE: 12

Trp Tyr Gln Gln Lys Pro Gly Ser Ser Pro Lys Pro Trp Ile Tyr
1               5                   10                  15

<210> SEQ ID NO 13
<211> LENGTH: 116
<212> TYPE: PRT
<213> ORGANISM: mouse

<400> SEQUENCE: 13

Ser Gly Pro Gly Ile Leu Gln Pro Ser Gln Thr Leu Ser Leu Thr Cys
1               5                   10                  15

Ser Phe Ser Gly Phe Ser Leu Tyr Thr Phe Asp Met Gly Val Gly Trp
            20                  25                  30

Ile Arg Gln Pro Ser Gly Lys Gly Leu Glu Trp Leu Ala His Ile Trp
        35                  40                  45

Trp Asp Asp Asp Lys Tyr Tyr Asn Pro Ala Leu Lys Ser Arg Leu Thr
    50                  55                  60

Val Ser Lys Asp Thr Ser Lys Asn Gln Val Phe Leu Lys Ile Pro Asn
65                  70                  75                  80

Val Asp Thr Ala Asp Ser Ala Thr Tyr Tyr Cys Ala Arg Val Arg Gly
                85                  90                  95

Leu His Asp Tyr Tyr Tyr Trp Phe Ala Tyr Trp Gly Gln Gly Thr Leu
            100                 105                 110

Val Thr Val Ser
            115

<210> SEQ ID NO 14
<211> LENGTH: 94
```

<212> TYPE: PRT
<213> ORGANISM: mouse

<400> SEQUENCE: 14

Ala Ser Pro Gly Glu Lys Val Thr Met Thr Cys Arg Ala Ser Ser Ser
1               5                   10                  15

Val Ser Tyr Met His Trp Tyr Gln Gln Lys Pro Gly Ser Ser Pro Lys
            20                  25                  30

Pro Trp Ile Tyr Ala Thr Ser Asn Leu Ala Ser Gly Val Pro Ala Arg
        35                  40                  45

Phe Ser Gly Ser Gly Ser Gly Thr Ser Tyr Ser Leu Thr Ile Ser Arg
    50                  55                  60

Val Glu Ala Glu Asp Ala Ala Thr Tyr Phe Cys Gln Gln Trp Ser Arg
65                  70                  75                  80

Asn Pro Phe Thr Phe Gly Ser Gly Thr Lys Leu Glu Ile Arg
                85                  90

<210> SEQ ID NO 15
<211> LENGTH: 8
<212> TYPE: PRT
<213> ORGANISM: mouse

<400> SEQUENCE: 15

Tyr Thr Phe Asp Met Gly Val Gly
1               5

<210> SEQ ID NO 16
<211> LENGTH: 16
<212> TYPE: PRT
<213> ORGANISM: mouse

<400> SEQUENCE: 16

His Ile Trp Trp Asp Asp Lys Tyr Tyr Asn Pro Ala Leu Lys Ser
1               5                   10                  15

<210> SEQ ID NO 17
<211> LENGTH: 13
<212> TYPE: PRT
<213> ORGANISM: mouse

<400> SEQUENCE: 17

Val Arg Gly Leu His Asp Tyr Tyr Tyr Trp Phe Ala Tyr
1               5                   10

<210> SEQ ID NO 18
<211> LENGTH: 10
<212> TYPE: PRT
<213> ORGANISM: mouse

<400> SEQUENCE: 18

Arg Ala Ser Ser Ser Val Ser Tyr Met His
1               5                   10

<210> SEQ ID NO 19
<211> LENGTH: 7
<212> TYPE: PRT
<213> ORGANISM: mouse

<400> SEQUENCE: 19

Ala Thr Ser Asn Leu Ala Ser
1               5

```
<210> SEQ ID NO 20
<211> LENGTH: 9
<212> TYPE: PRT
<213> ORGANISM: mouse

<400> SEQUENCE: 20

Gln Gln Trp Ser Arg Asn Pro Phe Thr
1               5

<210> SEQ ID NO 21
<211> LENGTH: 116
<212> TYPE: PRT
<213> ORGANISM: mouse

<400> SEQUENCE: 21

Ser Gly Pro Gly Ile Leu Gln Pro Ser Gln Thr Leu Ser Leu Thr Cys
1               5                   10                  15

Ser Phe Ser Gly Phe Ser Leu Tyr Thr Phe Asp Met Gly Val Gly Trp
                20                  25                  30

Ile Arg Gln Pro Ser Gly Lys Gly Leu Glu Trp Leu Ala Gln Ile Trp
            35                  40                  45

Trp Asp Asp Lys Tyr Tyr Asn Pro Gly Leu Lys Ser Arg Leu Thr
    50                  55                  60

Ile Ser Lys Asp Thr Ser Lys Asn Gln Val Phe Leu Lys Ile Pro Asn
65                  70                  75                  80

Val Asp Thr Ala Asp Ser Ala Thr Tyr Tyr Cys Ala Arg Ile Arg Gly
                85                  90                  95

Leu Arg Asp Tyr Tyr Tyr Trp Phe Ala Tyr Trp Gly Gln Gly Thr Leu
                100                 105                 110

Val Thr Val Ser
        115

<210> SEQ ID NO 22
<211> LENGTH: 94
<212> TYPE: PRT
<213> ORGANISM: mouse

<400> SEQUENCE: 22

Ala Ser Pro Gly Glu Lys Val Thr Met Thr Cys Arg Ala Ser Ser Ser
1               5                   10                  15

Val Ser Tyr Met His Trp Tyr Gln Gln Lys Pro Gly Ser Ser Pro Lys
                20                  25                  30

Pro Trp Ile Tyr Ala Thr Ser Asn Leu Ala Ser Gly Val Pro Ala Arg
            35                  40                  45

Phe Ser Gly Ser Gly Ser Gly Thr Ser Tyr Ser Leu Thr Ile Ser Arg
    50                  55                  60

Val Glu Ala Glu Asp Ala Ala Thr Tyr Phe Cys Gln Gln Trp Ser Arg
65                  70                  75                  80

Asn Pro Phe Thr Phe Gly Ser Gly Thr Lys Leu Glu Ile Arg
                85                  90

<210> SEQ ID NO 23
<211> LENGTH: 8
<212> TYPE: PRT
<213> ORGANISM: mouse

<400> SEQUENCE: 23

Tyr Thr Phe Asp Met Gly Val Gly
1               5
```

<210> SEQ ID NO 24
<211> LENGTH: 16
<212> TYPE: PRT
<213> ORGANISM: mouse

<400> SEQUENCE: 24

Gln Ile Trp Trp Asp Asp Lys Tyr Tyr Asn Pro Gly Leu Lys Ser
1               5                   10                  15

<210> SEQ ID NO 25
<211> LENGTH: 13
<212> TYPE: PRT
<213> ORGANISM: mouse

<400> SEQUENCE: 25

Ile Arg Gly Leu Arg Asp Tyr Tyr Tyr Trp Phe Ala Tyr
1               5                   10

<210> SEQ ID NO 26
<211> LENGTH: 10
<212> TYPE: PRT
<213> ORGANISM: mouse

<400> SEQUENCE: 26

Arg Ala Ser Ser Ser Val Ser Tyr Met His
1               5                   10

<210> SEQ ID NO 27
<211> LENGTH: 7
<212> TYPE: PRT
<213> ORGANISM: mouse

<400> SEQUENCE: 27

Ala Thr Ser Asn Leu Ala Ser
1               5

<210> SEQ ID NO 28
<211> LENGTH: 9
<212> TYPE: PRT
<213> ORGANISM: mouse

<400> SEQUENCE: 28

Gln Gln Trp Ser Arg Asn Pro Phe Thr
1               5

<210> SEQ ID NO 29
<211> LENGTH: 117
<212> TYPE: PRT
<213> ORGANISM: mouse

<400> SEQUENCE: 29

Ser Gly Pro Gly Ile Leu Gln Pro Ser Gln Thr Leu Ser Leu Thr Cys
1               5                   10                  15

Ser Phe Ser Gly Phe Ser Leu Ser Thr Phe Gly Leu Gly Val Gly Trp
                20                  25                  30

Ile Arg Gln Pro Ser Gly Lys Gly Leu Glu Trp Leu Ala His Ile Trp
                35                  40                  45

Trp Asp Asp Lys Ser Tyr Asn Pro Ala Leu Lys Ser Arg Leu Thr
        50                  55                  60

Ile Ser Lys Asp Thr Ser Lys Asn Gln Val Phe Leu Met Ile Ala Asn
65                  70                  75                  80

Val Asp Thr Ala Asp Thr Ala Thr Tyr Tyr Cys Ala Arg Ile Gly Pro

```
                    85                  90                  95

Lys Trp Ser Asn Tyr Tyr Tyr Cys Asp Tyr Trp Gly Gln Gly Thr
                100                 105                 110

Thr Leu Thr Val Ser
            115

<210> SEQ ID NO 30
<211> LENGTH: 94
<212> TYPE: PRT
<213> ORGANISM: mouse

<400> SEQUENCE: 30

Ala Ser Pro Gly Glu Lys Val Thr Met Thr Cys Arg Ala Ser Ser
1               5                  10                  15

Val Ser Tyr Met His Trp Tyr Gln Gln Lys Pro Gly Ser Ser Pro Lys
                20                  25                  30

Pro Tyr Ile Tyr Ala Thr Ser Asn Leu Ser Ser Gly Val Pro Ala Arg
            35                  40                  45

Phe Ser Gly Ser Gly Ser Gly Thr Ser Tyr Ser Leu Thr Ile Ser Arg
    50                  55                  60

Val Glu Ala Glu Asp Ala Ala Thr Tyr Tyr Cys Gln Gln Trp Ser Ser
65                  70                  75                  80

Asn Pro Phe Thr Phe Gly Ser Gly Thr Lys Leu Glu Ile Lys
                85                  90

<210> SEQ ID NO 31
<211> LENGTH: 8
<212> TYPE: PRT
<213> ORGANISM: mouse

<400> SEQUENCE: 31

Ser Thr Phe Gly Leu Gly Val Gly
1               5

<210> SEQ ID NO 32
<211> LENGTH: 16
<212> TYPE: PRT
<213> ORGANISM: mouse

<400> SEQUENCE: 32

His Ile Trp Trp Asp Asp Asp Lys Ser Tyr Asn Pro Ala Leu Lys Ser
1               5                  10                  15

<210> SEQ ID NO 33
<211> LENGTH: 14
<212> TYPE: PRT
<213> ORGANISM: mouse

<400> SEQUENCE: 33

Ile Gly Pro Lys Trp Ser Asn Tyr Tyr Tyr Tyr Cys Asp Tyr
1               5                  10

<210> SEQ ID NO 34
<211> LENGTH: 10
<212> TYPE: PRT
<213> ORGANISM: mouse

<400> SEQUENCE: 34

Arg Ala Ser Ser Ser Val Ser Tyr Met His
1               5                  10
```

```
<210> SEQ ID NO 35
<211> LENGTH: 7
<212> TYPE: PRT
<213> ORGANISM: mouse

<400> SEQUENCE: 35

Ala Thr Ser Asn Leu Ser Ser
1               5

<210> SEQ ID NO 36
<211> LENGTH: 9
<212> TYPE: PRT
<213> ORGANISM: mouse

<400> SEQUENCE: 36

Gln Gln Trp Ser Ser Asn Pro Phe Thr
1               5

<210> SEQ ID NO 37
<211> LENGTH: 117
<212> TYPE: PRT
<213> ORGANISM: mouse

<400> SEQUENCE: 37

Ser Gly Pro Gly Ile Leu Gln Pro Ser Gln Thr Leu Ser Leu Thr Cys
1               5                   10                  15

Ser Phe Ser Gly Phe Ser Leu Ser Thr Phe Gly Leu Gly Val Gly Trp
            20                  25                  30

Ile Arg Gln Pro Ser Gly Lys Gly Leu Glu Trp Leu Ala His Ile Trp
        35                  40                  45

Trp Asp Asp Asp Lys Ser Tyr Asn Pro Ala Leu Lys Ser Gln Leu Thr
    50                  55                  60

Ile Ser Lys Asp Thr Ser Lys Asn Gln Val Leu Leu Lys Ile Ala Asn
65                  70                  75                  80

Val Asp Thr Ala Asp Thr Ala Thr Tyr Tyr Cys Ala Arg Ile Gly Pro
                85                  90                  95

Lys Trp Ser Asn Tyr Tyr Tyr Tyr Cys Asp Tyr Trp Gly Gln Gly Thr
            100                 105                 110

Thr Leu Thr Val Ser
        115

<210> SEQ ID NO 38
<211> LENGTH: 94
<212> TYPE: PRT
<213> ORGANISM: mouse

<400> SEQUENCE: 38

Ala Ser Pro Gly Glu Lys Val Thr Met Thr Cys Arg Ala Ser Ser Ser
1               5                   10                  15

Val Ser Tyr Met His Trp Tyr Gln Gln Lys Pro Gly Ser Ser Pro Lys
            20                  25                  30

Pro Tyr Ile Tyr Ala Thr Ser Asn Leu Ser Ser Gly Val Pro Ala Arg
        35                  40                  45

Phe Ser Gly Ser Gly Ser Gly Thr Ser Tyr Ser Leu Thr Ile Ser Arg
    50                  55                  60

Val Glu Ala Glu Asp Ala Ala Thr Tyr Tyr Cys Gln Gln Trp Ser Ser
65                  70                  75                  80

Asn Pro Phe Thr Phe Gly Ser Gly Thr Lys Leu Glu Ile Lys
                85                  90
```

```
<210> SEQ ID NO 39
<211> LENGTH: 8
<212> TYPE: PRT
<213> ORGANISM: mouse

<400> SEQUENCE: 39

Ser Thr Phe Gly Leu Gly Val Gly
1               5

<210> SEQ ID NO 40
<211> LENGTH: 16
<212> TYPE: PRT
<213> ORGANISM: mouse

<400> SEQUENCE: 40

His Ile Trp Trp Asp Asp Asp Lys Ser Tyr Asn Pro Ala Leu Lys Ser
1               5                   10                  15

<210> SEQ ID NO 41
<211> LENGTH: 14
<212> TYPE: PRT
<213> ORGANISM: mouse

<400> SEQUENCE: 41

Ile Gly Pro Lys Trp Ser Asn Tyr Tyr Tyr Tyr Cys Asp Tyr
1               5                   10

<210> SEQ ID NO 42
<211> LENGTH: 10
<212> TYPE: PRT
<213> ORGANISM: mouse

<400> SEQUENCE: 42

Arg Ala Ser Ser Ser Val Ser Tyr Met His
1               5                   10

<210> SEQ ID NO 43
<211> LENGTH: 7
<212> TYPE: PRT
<213> ORGANISM: mouse

<400> SEQUENCE: 43

Ala Thr Ser Asn Leu Ser Ser
1               5

<210> SEQ ID NO 44
<211> LENGTH: 9
<212> TYPE: PRT
<213> ORGANISM: mouse

<400> SEQUENCE: 44

Gln Gln Trp Ser Ser Asn Pro Phe Thr
1               5

<210> SEQ ID NO 45
<211> LENGTH: 24
<212> TYPE: DNA
<213> ORGANISM: mouse

<400> SEQUENCE: 45
tacacttttg atatgggtgt aggc                                          24

<210> SEQ ID NO 46
<211> LENGTH: 48
```

```
<212> TYPE: DNA
<213> ORGANISM: mouse

<400> SEQUENCE: 46
cacatttggt gggatgatga taagtactat aacccagccc tgaagagt            48

<210> SEQ ID NO 47
<211> LENGTH: 40
<212> TYPE: DNA
<213> ORGANISM: mouse

<400> SEQUENCE: 47
gtaaggggcc tccatgatta ttactactgg ttttgcttac                     40

<210> SEQ ID NO 48
<211> LENGTH: 30
<212> TYPE: DNA
<213> ORGANISM: mouse

<400> SEQUENCE: 48
agggccagtt caagtgtaag ttacatgcac                                30

<210> SEQ ID NO 49
<211> LENGTH: 21
<212> TYPE: DNA
<213> ORGANISM: mouse

<400> SEQUENCE: 49
gccacatcca acctggcgtc t                                         21

<210> SEQ ID NO 50
<211> LENGTH: 27
<212> TYPE: DNA
<213> ORGANISM: mouse

<400> SEQUENCE: 50
cagcagtgga gtcgaaaccc attcacg                                   27

<210> SEQ ID NO 51
<211> LENGTH: 348
<212> TYPE: DNA
<213> ORGANISM: mouse

<400> SEQUENCE: 51
tctggccctg ggatattgca gccctcccag accctcagtc tgacttgttc tttctctgga    60
ttttcactgt acacttttga tatgggtgta ggctggattc gtcagccttc agggaagggt   120
ctggagtggc tggcacacat tggtgggat gatgataagt actataaccc agccctgaag   180
agtcggctca cagtctccaa ggatacctcc aaaaaccagg tcttcctcaa gatccccaat   240
gtggacactg cagatagtgc cacatactac tgtgctcgag taaggggcct ccatgattat   300
tactactggt ttgcttactg gggccaaggg actctggtca ctgtctct              348

<210> SEQ ID NO 52
<211> LENGTH: 282
<212> TYPE: DNA
<213> ORGANISM: mouse

<400> SEQUENCE: 52
gcatctccag gggagaaggt cacaatgact tgcagggcca gttcaagtgt aagttacatg    60
cactggtacc agcagaagcc aggatcctcc cccaaaccct ggatttatgc cacatccaac   120
```

```
ctggcgtctg gagtccctgc tcgcttcagt ggcagtgggt ctgggacctc ttactctctc      180
acaatcagca gagtggaggc tgaagatgct gccacttatt tctgccagca gtggagtcga      240
aacccattca cgttcggctc ggggacaaag ttggaaataa ga                         282
```

<210> SEQ ID NO 53
<211> LENGTH: 24
<212> TYPE: DNA
<213> ORGANISM: mouse

<400> SEQUENCE: 53

```
tacacttttg atatgggtgt aggc                                              24
```

<210> SEQ ID NO 54
<211> LENGTH: 48
<212> TYPE: DNA
<213> ORGANISM: mouse

<400> SEQUENCE: 54

```
cacatttggt gggatgatga taagtactat aacccagccc tgaagagt                    48
```

<210> SEQ ID NO 55
<211> LENGTH: 39
<212> TYPE: DNA
<213> ORGANISM: mouse

<400> SEQUENCE: 55

```
gtaaggggcc tccatgatta ttactactgg tttgcttac                              39
```

<210> SEQ ID NO 56
<211> LENGTH: 30
<212> TYPE: DNA
<213> ORGANISM: mouse

<400> SEQUENCE: 56

```
agggccagtt caagtgtaag ttacatgcac                                        30
```

<210> SEQ ID NO 57
<211> LENGTH: 21
<212> TYPE: DNA
<213> ORGANISM: mouse

<400> SEQUENCE: 57

```
gccacatcca acctggcgtc t                                                 21
```

<210> SEQ ID NO 58
<211> LENGTH: 27
<212> TYPE: DNA
<213> ORGANISM: mouse

<400> SEQUENCE: 58

```
cagcagtgga gtcgaaaccc attcacg                                           27
```

<210> SEQ ID NO 59
<211> LENGTH: 348
<212> TYPE: DNA
<213> ORGANISM: mouse

<400> SEQUENCE: 59

```
tctggccctg ggatattgca gccctccag accctcagtc tgacttgttc tttctctgga        60
ttttcactgt acacttttga tatgggtgta ggctggattc gtcagccttc agggaagggt      120
ctggagtggc tggcacaaat tggtgggat gatgataagt actataaccc aggcctgaag       180
```

```
agtcggctca caatctccaa ggatacctcc aaaaaccagg tattcctcaa gatccccaat    240
gtggacactg cagatagtgc cacatactac tgtgctcgaa taaggggcct ccgtgattat    300
tactactggt ttgcttactg gggccaaggg actctggtca ctgtctct                348
```

<210> SEQ ID NO 60
<211> LENGTH: 282
<212> TYPE: DNA
<213> ORGANISM: mouse

<400> SEQUENCE: 60

```
gcatctccag gggagaaggt cacaatgact tgcagggcca gctcaagtgt aagttacatg     60
cactggtacc agcagaagcc aggatcctcc cccaaaccct ggatttatgc cacatccaac    120
ctggcttctg gagtccctgc tcgcttcagt ggcagtgggt ctgggacctc ttactctctc    180
acaatcagca gagtggaggc tgaagatgct gccacttatt tctgccagca gtggagtcga    240
aacccattca cgttcggctc ggggacaaag ttggaaataa ga                       282
```

<210> SEQ ID NO 61
<211> LENGTH: 24
<212> TYPE: DNA
<213> ORGANISM: mouse

<400> SEQUENCE: 61

```
tacacttttg atatgggtgt aggc                                            24
```

<210> SEQ ID NO 62
<211> LENGTH: 48
<212> TYPE: DNA
<213> ORGANISM: mouse

<400> SEQUENCE: 62

```
caaatttggt gggatgatga taagtactat aacccaggcc tgaagagt                  48
```

<210> SEQ ID NO 63
<211> LENGTH: 39
<212> TYPE: DNA
<213> ORGANISM: mouse

<400> SEQUENCE: 63

```
ataaggggcc tccgtgatta ttactactgg tttgcttac                            39
```

<210> SEQ ID NO 64
<211> LENGTH: 30
<212> TYPE: DNA
<213> ORGANISM: mouse

<400> SEQUENCE: 64

```
agggccagct caagtgtaag ttacatgcac                                      30
```

<210> SEQ ID NO 65
<211> LENGTH: 21
<212> TYPE: DNA
<213> ORGANISM: mouse

<400> SEQUENCE: 65

```
gccacatcca acctggcttc t                                               21
```

<210> SEQ ID NO 66
<211> LENGTH: 27
<212> TYPE: DNA

<213> ORGANISM: mouse

<400> SEQUENCE: 66
cagcagtgga gtcgaaaccc attcacg         27

<210> SEQ ID NO 67
<211> LENGTH: 351
<212> TYPE: DNA
<213> ORGANISM: mouse

<400> SEQUENCE: 67
tctggccctg ggatattgca gccctcccag accctcagtc tgacttgttc tttctctggg     60
ttttcgctga gcactttggg tttgggtgta ggctggattc gtcagccttc agggaagggt    120
ctggagtggc tggcacacat tggtgggat gatgataagt cctataaccc agccctgaag     180
agtcggctca caatctccaa ggatacctcc aaaaaccagg tcttcctcat gatcgccaat    240
gtggacactg cagatactgc cacatactac tgtgctcgaa taggcccgaa atggagcaac    300
tactactact actgtgacta ctggggccaa ggcaccactc tcacagtctc c             351

<210> SEQ ID NO 68
<211> LENGTH: 282
<212> TYPE: DNA
<213> ORGANISM: mouse

<400> SEQUENCE: 68
gcatctccag gggagaaggt cacaatgact tgcagggcca gctcaagtgt tagttacatg     60
cactggtacc agcagaagcc aggatcctcc cccaaaccct acatttatgc cacatccaac    120
ctgtcttctg gagtccctgc tcgcttcagt ggcagtgggt ctgggacctc ttactctctc    180
acaatcagca gtgtggaggc tgaagatgct gccacttatt actgccagca gtggagtagt    240
aaccccttca cgttcggctc ggggacaaag ttggaaataa aa                       282

<210> SEQ ID NO 69
<211> LENGTH: 24
<212> TYPE: DNA
<213> ORGANISM: mouse

<400> SEQUENCE: 69
agcacttttg gtttgggtgt aggc            24

<210> SEQ ID NO 70
<211> LENGTH: 48
<212> TYPE: DNA
<213> ORGANISM: mouse

<400> SEQUENCE: 70
cacatttggt gggatgatga taagtcctat aacccagccc tgaagagt     48

<210> SEQ ID NO 71
<211> LENGTH: 42
<212> TYPE: DNA
<213> ORGANISM: mouse

<400> SEQUENCE: 71
ataggcccga aatggagcaa ctactactac tactgtgact ac           42

<210> SEQ ID NO 72
<211> LENGTH: 30
<212> TYPE: DNA
<213> ORGANISM: mouse

<400> SEQUENCE: 72
agggccagct caagtgttag ttacatgcac                                              30

<210> SEQ ID NO 73
<211> LENGTH: 21
<212> TYPE: DNA
<213> ORGANISM: mouse

<400> SEQUENCE: 73
gccacatcca acctgtcttc t                                                       21

<210> SEQ ID NO 74
<211> LENGTH: 27
<212> TYPE: DNA
<213> ORGANISM: mouse

<400> SEQUENCE: 74
cagcagtgga gtagtaaccc cttcacg                                                 27

<210> SEQ ID NO 75
<211> LENGTH: 351
<212> TYPE: DNA
<213> ORGANISM: mouse

<400> SEQUENCE: 75
tctggccctg ggatattgca gccctcccag accctcagtc tgacttgttc tttctctggg             60
ttttcgctga gcacttttgg tttgggtgta ggctggattc gtcagccttc agggaagggt            120
ctggagtggc tggcacacat tggtgggat gatgataagt cctataaccc agccctgaag             180
agtcagctca caatctccaa ggatacctcc aaaaaccagg tactcctcaa gatcgccaat            240
gtggacactg cagatactgc cacatactac tgtgctcgaa taggcccgaa atggagcaac            300
tactactact actgtgacta ctggggccaa ggcaccactc tcacagtctc c                    351

<210> SEQ ID NO 76
<211> LENGTH: 282
<212> TYPE: DNA
<213> ORGANISM: mouse

<400> SEQUENCE: 76
gcatctccag gggagaaggt cacaatgact tgcagggcca gctcaagtgt tagttacatg             60
cactggtacc agcagaagcc aggatcctcc cccaaaccct acatttatgc cacatccaac            120
ctgtcttctg gagtccctgc tcgcttcagt ggcagtggg ctgggacctc ttactctctc             180
acaatcagca gagtggaggc tgaagatgct gccacttatt actgccagca gtggagtagt            240
aaccccttca cgttcggctc ggggacaaag ttggaaataa aa                              282

<210> SEQ ID NO 77
<211> LENGTH: 24
<212> TYPE: DNA
<213> ORGANISM: mouse

<400> SEQUENCE: 77
agcacttttg gtttgggtgt aggc                                                    24

<210> SEQ ID NO 78
<211> LENGTH: 48
<212> TYPE: DNA
<213> ORGANISM: mouse

-continued

<400> SEQUENCE: 78
cacatttggt gggatgatga taagtcctat aacccagccc tgaagagt         48

<210> SEQ ID NO 79
<211> LENGTH: 42
<212> TYPE: DNA
<213> ORGANISM: mouse

<400> SEQUENCE: 79
ataggcccga aatggagcaa ctactactac tactgtgact ac               42

<210> SEQ ID NO 80
<211> LENGTH: 30
<212> TYPE: DNA
<213> ORGANISM: mouse

<400> SEQUENCE: 80
agggccagct caagtgttag ttacatgcac                             30

<210> SEQ ID NO 81
<211> LENGTH: 21
<212> TYPE: DNA
<213> ORGANISM: mouse

<400> SEQUENCE: 81
gccacatcca acctgtcttc t                                      21

<210> SEQ ID NO 82
<211> LENGTH: 27
<212> TYPE: DNA
<213> ORGANISM: mouse

<400> SEQUENCE: 82
cagcagtgga gtagtaaccc cttcacg                                27

<210> SEQ ID NO 83
<211> LENGTH: 23
<212> TYPE: PRT
<213> ORGANISM: mouse

<400> SEQUENCE: 83

Ser Gly Pro Gly Ile Leu Gln Pro Ser Gln Thr Leu Ser Leu Thr Cys
1               5                   10                  15

Ser Phe Ser Gly Phe Ser Leu
            20

<210> SEQ ID NO 84
<211> LENGTH: 11
<212> TYPE: PRT
<213> ORGANISM: mouse

<400> SEQUENCE: 84

Ala Ser Pro Gly Glu Lys Val Thr Met Thr Cys
1               5                   10

<210> SEQ ID NO 85
<211> LENGTH: 32
<212> TYPE: PRT
<213> ORGANISM: mouse

<400> SEQUENCE: 85

Arg Leu Thr Val Ser Lys Asp Thr Ser Lys Asn Gln Val Phe Leu Lys
1               5                   10                  15

```
Ile Pro Asn Val Asp Thr Ala Asp Ser Ala Thr Tyr Tyr Cys Ala Arg
            20                  25                  30
```

<210> SEQ ID NO 86
<211> LENGTH: 32
<212> TYPE: PRT
<213> ORGANISM: mouse

<400> SEQUENCE: 86

```
Gly Val Pro Ala Arg Phe Ser Gly Ser Gly Ser Gly Thr Ser Tyr Ser
1               5                   10                  15

Leu Thr Ile Ser Arg Val Glu Ala Glu Asp Ala Ala Thr Tyr Phe Cys
            20                  25                  30
```

<210> SEQ ID NO 87
<211> LENGTH: 23
<212> TYPE: PRT
<213> ORGANISM: artificial sequence
<220> FEATURE:
<223> OTHER INFORMATION: human-mouse sequence

<400> SEQUENCE: 87

```
Ser Gly Pro Thr Leu Val Lys Pro Thr Gln Thr Leu Thr Leu Thr Cys
1               5                   10                  15

Thr Phe Ser Gly Phe Ser Leu
            20
```

<210> SEQ ID NO 88
<211> LENGTH: 11
<212> TYPE: PRT
<213> ORGANISM: artificial sequence
<220> FEATURE:
<223> OTHER INFORMATION: human-mouse sequence

<400> SEQUENCE: 88

```
Leu Ser Pro Gly Glu Arg Ala Thr Leu Ser Cys
1               5                   10
```

<210> SEQ ID NO 89
<211> LENGTH: 32
<212> TYPE: PRT
<213> ORGANISM: artificial sequence
<220> FEATURE:
<223> OTHER INFORMATION: human-mouse sequence

<400> SEQUENCE: 89

```
Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Arg
            20                  25                  30
```

<210> SEQ ID NO 90
<211> LENGTH: 32
<212> TYPE: PRT
<213> ORGANISM: artificial sequence
<220> FEATURE:
<223> OTHER INFORMATION: human-mouse sequence

<400> SEQUENCE: 90

```
Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30
```

ANTIBODIES, PHARMACEUTICAL COMPOSITIONS AND USES THEREOF

CROSS-REFERENCE TO RELATED APPLICATIONS

The present application is a National Stage Application of PCT/US2015/025305, filed. Apr. 10, 2015, which claims the benefit of U.S. Patent Application No. 61/977,824, filed on Apr. 10, 2014, and U.S. Patent Application No. 62/057,381, filed on Sep. 30, 2014. The entirety of the aforementioned applications is incorporated herein by reference.

FIELD

The present invention relates to antibodies to tumor-associated carbohydrate antigens, including specific portions or variants specific for at least one tumor-associated carbohydrate antigen or fragment thereof, as well as nucleic acids encoding such antibodies, complementary nucleic acids, vectors, host cells and methods of making and using thereof, including therapeutic formulations and pharmaceutical compositions comprising the antibody. Further, methods are provided for administering antibodies to a subject in an amount effective to inhibit cancer cells.

BACKGROUND

Numerous surface carbohydrates are expressed in malignant tumor cells. For example, Globo H (Fuc α1-->2Galβ1-->3GalNAcβ1-->3Gal α1-->4Galβ1-->4Glc) has been shown to be overexpressed on a variety of epithelial cancers and is associated with tumor aggressiveness and poor prognosis in breast cancer and small cell lung carcinoma. Previous studies have shown that Globo H and Stage-specific embryonic antigen 3 (SSEA3, also called Gb5) were observed on breast cancer cells and breast cancer stem cells (W W Chang et al. "Expression of Globo H and SSEA3 in breast cancer stem cells and the involvement of fucosyl transferases 1 and 2 in Globo H synthesis. PNAS, 105(33): 11667-11672).

These findings support a rationale for the development of antibodies to tumor associated carbohydrate antigens, as there is still an unmet need for effective treatment and/or prevention for cancer. The present invention provides antibodies to tumor associated carbohydrate antiges to satisfy these and other needs.

SUMMARY OF THE INVENTION

The present invention provides for antibodies, or antigen-binding portions thereof, comprising a variable domain that bind to a carbohydrate antigen, conjugated versions of these antibodies, encoding or complementary nucleic acids, vectors, host cells, compositions, formulations, devices, transgenic animals, transgenic plants related thereto, and methods of making and using thereof, as described and enabled herein, in combination with what is known in the art. The antibody or antigen-binding portion thereof may have a dissociation constant ($K_D$) of about 10E-7 M or less, about 10E-8 M or less, about 10E-9 M or less, about 10E-10 M or less, about 10E-11 M or less, or about 10E-12 M or less. The antibody or antigen-binding portion thereof may be humanized or chimeric.

In one embodiment, the present invention provides for an antibody, or an antigen-binding portion thereof, comprising a heavy chain variable domain comprising an amino acid sequence about 80% to about 100% homologous to the amino acid sequence shown in SEQ ID NO: 3

In another embodiment, the present invention provides for an antibody, or an antigen-binding portion thereof, comprising a light chain variable domain comprising an amino acid sequence about 80% to about 100% homologous to the amino acid sequence shown in SEQ ID NO: 4.

In yet another embodiment, the present invention provides for an antibody, or an antigen-binding portion thereof, comprising a heavy chain variable domain comprising an amino acid sequence about 80% to about 100% homologous to the amino acid sequence shown in SEQ ID NO: 3; and a light chain variable domain comprising an amino acid sequence about 80% to about 100% homologous to the amino acid sequence shown in SEQ ID NO: 4.

In a fourth embodiment, the present invention provides an antibody, or an antigen-binding portion thereof, comprises a heavy chain region, wherein the heavy chain region comprises three complementarity determining regions (CDRs), CDR1, CDR2 and CDR3, having amino acid sequences about 80% to about 100% homologous to the amino acid sequences set forth in SEQ ID NOs: 5, 6 and 7, respectively. In an exemplary embodiment, the heavy chain further comprises a framework between a leader sequence and said CDR1 having an amino acid sequence about 80% to about 100% homologous to SEQ ID NO: 87. In another embodiment, the heavy chain further comprises a framework between said CDR2 and said CDR3 having an amino acid sequence about 80% to about 100% homologous to SEQ ID NO: 89. In yet another exemplary embodiment, the heavy chain further comprises a framework between said CDR1 and said CDR2 of the heavy chain having amino acid sequence about 80% to about 100% homologous to SEQ ID NO: 11, wherein the framework contains glycine at position 9 and the antibody or the antigen-binding portion thereof binds to a carbohydrate antigen, such as Globo H.

In a fifth embodiment, the present invention provides an antibody, or an antigen-binding portion thereof, comprises a light chain region, wherein the light chain region comprises three CDRs, CDR1, CDR2 and CDR3, having amino acid sequences about 80% to about 100% homologous to the amino acid sequences set forth in SEQ ID NOs: 8, 9 and 10, respectively. In an exemplary embodiment, the light chain further comprises a framework between a leader sequence and said CDR1 having an amino acid sequence about 80% to about 100% homologous to SEQ ID NO: 88. In another exemplary embodiment, the light chain further comprises a framework between said CDR2 and said CDR3 of the light chain, having an amino acid sequence about 80% to about 100% homologous to SEQ ID NO: 90. In yet another exemplary embodiment, the light chain further comprises a framework between said CDR1 and said CDR2 of the light chain having amino acid sequence about 80% to about 100% homologous to SEQ ID NO: 12, wherein the framework contains proline at position 12, and the antibody or the antigen-binding portion thereof binds to Globo H. In yet another exemplary embodiment, the light chain further comprises a framework between said CDR1 and said CDR2 of the light chain having amino acid sequence about 80% to about 100% homologous to SEQ ID NO: 12, wherein the framework contains tryptophan at position 13, and the antibody or the antigen-binding portion thereof binds to a carbohydrate antigen, such as Globo H.

In a sixth embodiment, the present invention provides an antibody, or an antigen-binding portion thereof, comprising a heavy chain region and a light chain region, wherein the heavy chain region comprises three CDRs, CDR1, CDR2 and CDR3, having amino acid sequences about 80% to about 100% homologous to the amino acid sequences set forth in SEQ ID NOs: 5, 6 and 7, respectively, and wherein the light chain region comprises three CDRs, CDR1, CDR2 and CDR3, having amino acid sequences about 80% to about 100% homologous to the amino acid sequences set forth in SEQ ID NOs: 8, 9 and 10, respectively.

In some embodiments, an antibody, or an antigen-binding portion thereof, comprising: a heavy chain region, wherein the heavy chain region comprises a CDR having an amino acid sequence about 80% to about 100% homologous to the amino acid sequence selected from SEQ ID NOs: 5, 6 or 7 are provided. In other embodiments, an antibody, or an antigen-binding portion thereof, comprising a light chain region, wherein the light chain region comprises a CDR having an amino acid sequence about 80% to about 100% homologous to the amino acid sequence selected from SEQ ID NOs: 8, 9 or 10 are provided.

The present invention is also directed to an antibody, or an antigen-binding portion thereof, comprising: a heavy chain variable domain comprising an amino acid sequence about 80% to about 100% homologous to the amino acid sequence shown in SEQ ID NO: 13.

The present invention is also directed to an antibody, or an antigen-binding portion thereof, comprising: a light chain variable domain comprising an amino acid sequence about 80% to about 100% homologous to the amino acid sequence shown in SEQ ID NO: 14.

The present invention is also directed to an antibody, or an antigen-binding portion thereof, comprising: a heavy chain variable domain comprising an amino acid sequence about 80% to about 100% homologous to the amino acid sequence shown in SEQ ID NO: 13; and a light chain variable domain comprising an amino acid sequence about 80% to about 100% homologous to the amino acid sequence shown in SEQ ID NO: 14.

An exemplary embodiment provides an antibody, or an antigen-binding portion thereof, comprises a heavy chain region, wherein the heavy chain region comprises three CDRs, CDR1, CDR2 and CDR3, having amino acid sequences about 80% to about 100% homologous to the amino acid sequences set forth in SEQ ID NOs: 15, 16 and 17, respectively. Another exemplary embodiment provides an antibody, or an antigen-binding portion thereof, comprises a light chain region, wherein the light chain region comprises three CDRs, CDR1, CDR2 and CDR3, having amino acid sequences about 80% to about 100% homologous to the amino acid sequences set forth in SEQ ID NOs: 18, 19 and 20, respectively.

Another exemplary embodiment provides an antibody, or an antigen-binding portion thereof, comprising a heavy chain region and a light chain region, wherein the heavy chain region comprises three CDRs, CDR1, CDR2 and CDR3, having amino acid sequences about 80% to about 100% homologous to the amino acid sequences set forth in SEQ ID NOs: 15, 16 and 17, respectively, and wherein the light chain region comprises three CDRs, CDR1, CDR2 and CDR3, having amino acid sequences about 80% to about 100% homologous to the amino acid sequences set forth in SEQ ID NOs: 18, 19 and 20, respectively.

In some embodiments, an antibody, or an antigen-binding portion thereof, comprising: a heavy chain region, wherein the heavy chain region comprises a CDR having an amino acid sequence about 80% to about 100% homologous to the amino acid sequence selected from SEQ ID NOs: 15, 16 or 17 are provided. In other embodiments, an antibody, or an antigen-binding portion thereof, comprising a light chain region, wherein the light chain region comprises a CDR having an amino acid sequence about 80% to about 100% homologous to the amino acid sequence selected from SEQ ID NOs: 18, 19 or 20 are provided.

One embodiment of the present invention is an antibody, or an antigen-binding portion thereof, comprising: a heavy chain variable domain comprising an amino acid sequence about 80% to about 100% homologous to the amino acid sequence shown in SEQ ID NO: 21.

Another embodiment of the present invention is an antibody, or an antigen-binding portion thereof, comprising: a light chain variable domain comprising an amino acid sequence about 80% to about 100% homologous to the amino acid sequence shown in SEQ ID NO: 22.

In yet another embodiment of the present invention is an antibody, or an antigen-binding portion thereof, comprising: a heavy chain variable domain comprising an amino acid sequence about 80% to about 100% homologous to the amino acid sequence shown in SEQ ID NO: 21; and a light chain variable domain comprising an amino acid sequence about 80% to about 100% homologous to the amino acid sequence shown in SEQ ID NO: 22.

An exemplary embodiment provides an antibody, or an antigen-binding portion thereof, comprises a heavy chain region, wherein the heavy chain region comprises three CDRs, CDR1, CDR2 and CDR3, having amino acid sequences about 80% to about 100% homologous to the amino acid sequences set forth in SEQ ID NOs: 23, 24 and 25, respectively. Another exemplary embodiment provides an antibody, or an antigen-binding portion thereof, comprises a light chain region, wherein the light chain region comprises three CDRs, CDR1, CDR2 and CDR3, having amino acid sequences about 80% to about 100% homologous to the amino acid sequences set forth in SEQ ID NOs: 26, 27 and 28, respectively.

Another exemplary embodiment provides an antibody, or an antigen-binding portion thereof, comprising a heavy chain region and a light chain region, wherein the heavy chain region comprises three CDRs, CDR1, CDR2 and CDR3, having amino acid sequences about 80% to about 100% homologous to the amino acid sequences set forth in SEQ ID NOs: 23, 24 and 25, respectively, and wherein the light chain region comprises three CDRs, CDR1, CDR2 and CDR3, having amino acid sequences about 80% to about 100% homologous to the amino acid sequences set forth in SEQ ID NOs: 26, 27 and 28, respectively.

In some embodiments, an antibody, or an antigen-binding portion thereof, comprising: a heavy chain region, wherein the heavy chain region comprises a CDR having an amino acid sequence about 80% to about 100% homologous to the amino acid sequence selected from SEQ ID NOs: 23, 24 or 25 are provided. In other embodiments, an antibody, or an antigen-binding portion thereof, comprising a light chain region, wherein the light chain region comprises a CDR having an amino acid sequence about 80% to about 100% homologous to the amino acid sequence selected from SEQ ID NOs: 26, 27 or 28 are provided.

The present invention also discloses an antibody, or an antigen-binding portion thereof, comprising: a heavy chain variable domain comprising an amino acid sequence about 80% to about 100% homologous to the amino acid sequence shown in SEQ ID NO: 29.

The present invention also discloses an antibody, or an antigen-binding portion thereof, comprising: a light chain variable domain comprising an amino acid sequence about 80% to about 100% homologous to the amino acid sequence shown in SEQ ID NO: 30.

The present invention also discloses an antibody, or an antigen-binding portion thereof, comprising: a heavy chain variable domain comprising an amino acid sequence about 80% to about 100% homologous to the amino acid sequence shown in SEQ ID NO: 29; and a light chain variable domain comprising an amino acid sequence about 80% to about 100% homologous to the amino acid sequence shown in SEQ ID NO: 30.

An exemplary embodiment provides an antibody, or an antigen-binding portion thereof, comprises a heavy chain region, wherein the heavy chain region comprises three CDRs, CDR1, CDR2 and CDR3, having amino acid sequences about 80% to about 100% homologous to the amino acid sequences set forth in SEQ ID NOs: 31, 32 and 33, respectively. Another exemplary embodiment provides an antibody, or an antigen-binding portion thereof, comprises a light chain region, wherein the light chain region comprises three CDRs, CDR1, CDR2 and CDR3, having amino acid sequences about 80% to about 100% homologous to the amino acid sequences set forth in SEQ ID NOs: 34, 35 and 36, respectively.

Another exemplary embodiment provides an antibody, or an antigen-binding portion thereof, comprising a heavy chain region and a light chain region, wherein the heavy chain region comprises three CDRs, CDR1, CDR2 and CDR3, having amino acid sequences about 80% to about 100% homologous to the amino acid sequences set forth in SEQ ID NOs: 31, 32 and 33, respectively, and wherein the light chain region comprises three CDRs, CDR1, CDR2 and CDR3, having amino acid sequences about 80% to about 100% homologous to the amino acid sequences set forth in SEQ ID NOs: 34, 35 and 36, respectively.

In some embodiments, an antibody, or an antigen-binding portion thereof, comprising: a heavy chain region, wherein the heavy chain region comprises a CDR having an amino acid sequence about 80% to about 100% homologous to the amino acid sequence selected from SEQ ID NOs: 31, 32 or 33 are provided. In other embodiments, an antibody, or an antigen-binding portion thereof, comprising a light chain region, wherein the light chain region comprises a CDR having an amino acid sequence about 80% to about 100% homologous to the amino acid sequence selected from SEQ ID NOs: 34, 35 or 36 are provided.

One embodiment of the present invention provides an antibody, or an antigen-binding portion thereof, comprising: a heavy chain variable domain comprising an amino acid sequence about 80% to about 100% homologous to the amino acid sequence shown in SEQ ID NO: 37.

Another embodiment of the present invention provides an antibody, or an antigen-binding portion thereof, comprising: a light chain variable domain comprising an amino acid sequence about 80% to about 100% homologous to the amino acid sequence shown in SEQ ID NO: 38.

Another embodiment of the present invention provides an antibody, or an antigen-binding portion thereof, comprising: a heavy chain variable domain comprising an amino acid sequence about 80% to about 100% homologous to the amino acid sequence shown in SEQ ID NO: 37; and a light chain variable domain comprising an amino acid sequence about 80% to about 100% homologous to the amino acid sequence shown in SEQ ID NO: 38.

An exemplary embodiment provides an antibody, or an antigen-binding portion thereof, comprises a heavy chain region, wherein the heavy chain region comprises three CDRs, CDR1, CDR2 and CDR3, having amino acid sequences about 80% to about 100% homologous to the amino acid sequences set forth in SEQ ID NOs: 39, 40 and 41, respectively. Another exemplary embodiment discloses an antibody, or an antigen-binding portion thereof, comprises a light chain region, wherein the light chain region comprises three CDRs, CDR1, CDR2 and CDR3, having amino acid sequences about 80% to about 100% homologous to the amino acid sequences set forth in SEQ ID NOs: 42, 43 and 44, respectively.

Another exemplary embodiment provides an antibody, or an antigen-binding portion thereof, comprising a heavy chain region and a light chain region, wherein the heavy chain region comprises three CDRs, CDR1, CDR2 and CDR3, having amino acid sequences about 80% to about 100% homologous to the amino acid sequences set forth in SEQ ID NOs: 39, 40 and 41, respectively, and wherein the light chain region comprises three CDRs, CDR1, CDR2 and CDR3, having amino acid sequences about 80% to about 100% homologous to the amino acid sequences set forth in SEQ ID NOs: 42, 43 and 44, respectively.

In some embodiments, an antibody, or an antigen-binding portion thereof, comprising: a heavy chain region, wherein the heavy chain region comprises a CDR having an amino acid sequence about 80% to about 100% homologous to the amino acid sequence selected from SEQ ID NOs: 39, 40 or 41 are provided. In other embodiments, an antibody, or an antigen-binding portion thereof, comprising a light chain region, wherein the light chain region comprises a CDR having an amino acid sequence about 80% to about 100% homologous to the amino acid sequence selected from SEQ ID NOs: 42, 43 or 44 are provided.

The present invention provides for a pharmaceutical composition comprising the antibody or antigen-binding portion thereof as described herein and at least one pharmaceutically acceptable carrier.

The present invention also provides for a method of inhibiting Globo H expressing cancer cells, comprising administering to a subject in need thereof an effective amount of the antibody or antigen-binding portion thereof described herein, wherein the Globo H expressing cancer cells are inhibited.

The present invention also provides for hybridoma clones designated as 2C2 (deposited at The American Type Culture Collection (ATCC), 10801 University Boulevard, Manassas, Va. 20110, USA, on Mar. 26, 2014, under ATCC Accession Number PTA-121138), 3D7 (deposited at ATCC, 10801 University Boulevard, Manassas, Va. 20110, USA, on May 29, 2014, under ATCC Accession Number PTA-121310), 7A11 (deposited at ATCC, 10801 University Boulevard, Manassas, Va. 0110, USA, on May 29, 2014, under ATCC Accession Number PTA-121311), 2F8 (deposited at ATCC, 10801 University Boulevard, Manassas, Va. 20110, USA, on Mar. 26, 2014, under ATCC Accession Number PTA-121137) and 1E1 (deposited at ATCC, 10801 University Boulevard, Manassas, Va. 20110, USA, on May 29, 2014, under ATCC Accession Number PTA-121312), and antibodies or antigen-binding portions produced therefrom.

DETAILED DESCRIPTION OF THE INVENTION

Figure 1:
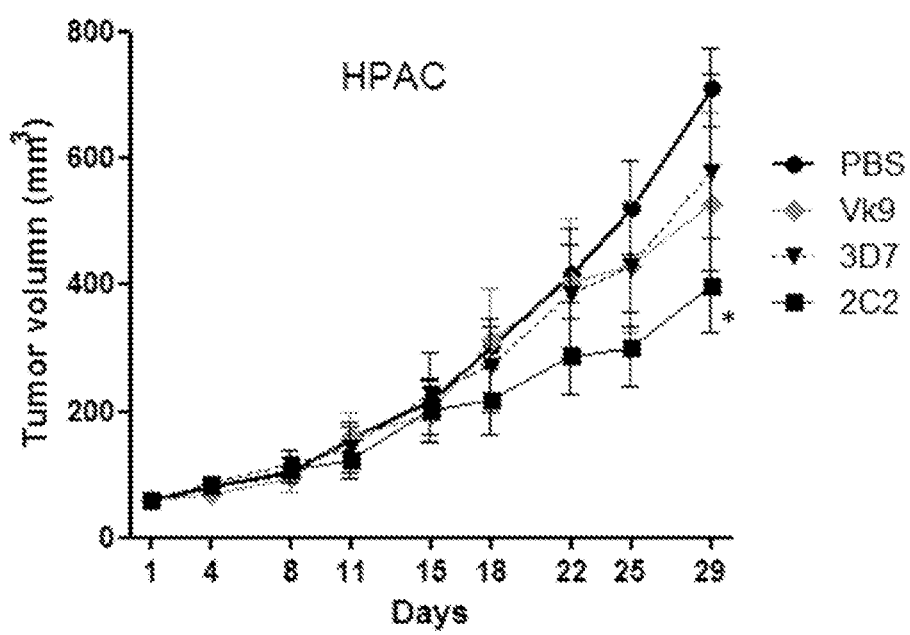
FIG. 1 is a linear plot showing the effect of PBS, Globo H-VK9 mAbs, Globo H-2C2 mAbs and Globo H-3D7 mAb on pancreatic cancer (HPAC) volume in mice.

As used herein, the articles "a" and "an" refer to one or more than one (i.e., at least one) of the grammatical object of the article. By way of example, "an element" means one element or more than one element.

An "effective amount," as used herein, refers to a dose of the vaccine or pharmaceutical composition that is sufficient to reduce the symptoms and signs of cancer, such as weight loss, pain and palpable mass, which is detectable, either clinically as a palpable mass or radiologically through various imaging means. The term "effective amount" and "therapeutically effective amount" are used interchangeably.

The term "subject" can refer to a vertebrate having cancer or to a vertebrate deemed to be in need of cancer treatment. Subjects include all warm-blooded animals, such as mammals, such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, mouse, rabbit, rat, gerbil, guinea pig, etc.). Thus, veterinary uses and medical formulations are contemplated herein.

All numbers herein are approximations and may be modified by "about."

The present invention provides for pharmaceutical compositions and methods for the treatment or inhibition of cancer cells. The pharmaceutical compositions comprises antibodies that recognize carbohydrate antigen, including mouse monoclonal antibodies, humanized antibodies, chimeric antibodies, or antigen-binding portions of any of the foregoing. These antibodies (or antigen-binding portion thereof) can neutralize the carbohydrate antigen, and/or inhibit cancer cells. Therefore, the present antibodies or antigen-binding portion thereof can be used in the treatment or inhibition of cancer cells.

Antibodies of the present invention include any protein or peptide that comprise at least one complementarity determining region (CDR) of a heavy or light chain, or a ligand binding portion thereof, derived from an antibody produced by the hybridoma designated 2C2 (deposited under ATCCAccession No.: PTA-121138), the hybridoma designated 3D7 (deposited under ATCCAccession No.: PTA-121310), the hybridoma designated 7A11 (deposited under ATCC Accession No.: PTA-121311), the hybridoma designated 2F8 (deposited under ATCC Accession No.: PTA-121137), or the hybridoma designated 1E1 (deposited under ATCC Accession No.: PTA-121312) as described herein. Antibodies include antibody fragments, antibody variants, monoclonal antibodies, polyclonal antibodies, and recombinant antibodies and the like. Antibodies can be generated in mice, rabbits or humans.

Antibodies of the present invention also include chimerized or humanized monoclonal antibodies generated from antibodies of the present invention.

Thus, anti-cancer antibodies of the present invention include in combination with a heavy chain or light chain variable region, a heavy chain or light chain constant region, a framework region, or any portion thereof, of non-murine origin, preferably of human origin, which can be incorporated into an antibody of the present invention.

Antibodies of the present invention are capable of modulating, decreasing, antagonizing, mitigating, alleviating, blocking, inhibiting, abrogating and/or interfering with at least one Globo-H expressing cancer cell activity in vitro, in situ and/or in vivo.

The term "antibody" is further intended to encompass antibodies, digestion fragments, specified portions and variants thereof, including antibody mimetics or comprising portions of antibodies that mimic the structure and/or function of an anti-cancer antibody or specified fragment or portion thereof, including single chain antibodies and fragments thereof, each containing at least one CDR derived from an anti-cancer antibody of the present invention. Functional fragments include antigen-binding fragments that bind to a Globo-H expressing cancer cells. For example, antibody fragments capable of binding to Globo-H expression cancer cells or portions thereof, including, but not limited to Fab (e.g., by papain digestion), Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

As used herein, 2C2 refers to the hybridoma clone or the antibodies generated by the corresponding hybridoma clone.

An antigen-binding portion of an antibody may include a portion of an antibody that specifically binds to a carbohydrate antigen (e.g., Globo H, SSEA-3 or SSEA-4).

The humanized antibody of the present invention is an antibody from a non-human species where the amino acid sequence in the non-antigen binding regions (and/or the antigen-binding regions) has been altered so that the antibody more closely resembles a human antibody while retaining its original binding ability.

Humanized antibodies can be generated by replacing sequences of the variable region that are not directly involved in antigen binding with equivalent sequences from human variable regions. Those methods include isolating, manipulating, and expressing the nucleic acid sequences that encode all or part of variable regions from at least one of a heavy or light chain. Sources of such nucleic acid are well known to those skilled in the art. The recombinant DNA encoding the humanized antibody, or fragment thereof, can then be cloned into an appropriate expression vector.

An antibody light or heavy chain variable region comprises a framework region interrupted by three hypervariable regions, referred to as CDRs. In one embodiment, humanized antibodies are antibody molecules from non-human species having one, two or all CDRs from the non-human species and one, two or all three framework regions from a human immunoglobulin molecule.

According to one aspect of the invention, the location of the CDRs and framework residues are determined by methods disclosed in Kabat, E. A., et al. (1991) Sequences of Proteins of Immunological Interest, Fifth Edition, U.S. Department of Health and Human Services, NIH Publication No. 91-3242. According to another aspect of the invention, the antibody or the antigen-binding portion thereof may have the following structure:

Leader Sequence-FW1-CDR1-FW2-CDR2-FW3-CDR3-in which the framework regions FW1, FW2, FW3 and the CDRs CDR1, CDR2, CDR3 have amino acid sequences disclosed in Table 1.

The humanized antibodies of the present invention can be produced by methods well known in the art. For example, once non-human (e.g., murine) antibodies are obtained, variable regions can be sequenced, and the location of the CDRs and framework residues determined. Kabat, E. A., et al. (1991) Sequences of Proteins of Immunological Interest, Fifth Edition, U.S. Department of Health and Human Services, NIH Publication No. 91-3242. Chothia, C. et al. (1987) J. Mol. Biol., 196:901-917. DNA encoding the light and heavy chain variable regions can, optionally, be ligated to corresponding constant regions and then subcloned into an appropriate expression vector. CDR-grafted antibody molecules can be produced by CDR-grafting or CDR substitution. One, two, or all CDRs of an immunoglobulin chain can be replaced. For example, all of the CDRs of a particular antibody may be from at least a portion of a non-human animal (e.g., mouse such as CDRs shown in Table 1) or only some of the CDRs may be replaced. It is only necessary to keep the CDRs required for binding of the antibody to a predetermined carbohydrate antigen (e.g., Globo H). Morrison, S. L., 1985, Science, 229:1202-1207. Oi et al., 1986, BioTechniques, 4:214. U.S. Pat. Nos. 5,585,089; 5,225,539; 5,693,761 and 5,693,762. EP 519596. Jones et al., 1986, Nature, 321:552-525. Verhoeyan et al., 1988, Science, 239: 1534. Beidler et al., 1988, J. Immunol., 141:4053-4060.

Also encompassed by the present invention are antibodies or antigen-binding portions thereof comprising one or two variable regions as disclosed herein, with the other regions replaced by sequences from at least one different species including, but not limited to, human, rabbits, sheep, dogs, cats, cows, horses, goats, pigs, monkeys, apes, gorillas, chimpanzees, ducks, geese, chickens, amphibians, reptiles and other animals.

A chimeric antibody is a molecule in which different portions are derived from different animal species. For example, an antibody may contain a variable region derived from a murine mAb and a human immunoglobulin constant region. Chimeric antibodies can be produced by recombinant DNA techniques. Morrison, et al., Proc Natl Acad Sci, 81:6851-6855 (1984). For example, a gene encoding a murine (or other species) antibody molecule is digested with restriction enzymes to remove the region encoding the murine Fc, and the equivalent portion of a gene encoding a human Fc constant region is then substituted into the recombinant DNA molecule. Chimeric antibodies can also be created by recombinant DNA techniques where DNA encoding murine V regions can be ligated to DNA encoding the human constant regions. Better et al., Science, 1988, 240: 1041-1043. Liu et al. PNAS, 1987 84:3439-3443. Liu et al., J. Immunol., 1987, 139:3521-3526. Sun et al. PNAS, 1987, 84:214-218. Nishimura et al., Canc. Res., 1987, 47:999-1005. Wood et al. Nature, 1985, 314:446-449. Shaw et al., J. Natl. Cancer Inst., 1988, 80:1553-1559. International Patent Publication Nos. WO1987002671 and WO 86/01533. European Patent Application Nos. 184, 187; 171, 496; 125, 023; and 173, 494. U.S. Pat. No. 4,816,567.

The antibodies can be full-length or can comprise a fragment (or fragments) of the antibody having an antigen-binding portion, including, but not limited to, Fab, F(ab')2, Fab', F(ab)', Fv, single chain Fv (scFv), bivalent scFv (bi-scFv), trivalent scFv (tri-scFv), Fd, dAb fragment (e.g., Ward et al., Nature, 341:544-546 (1989)), an isolated CDR, diabodies, triabodies, tetrabodies, linear antibodies, single-chain antibody molecules, and multispecific antibodies formed from antibody fragments. Single chain antibodies produced by joining antibody fragments using recombinant methods, or a synthetic linker, are also encompassed by the present invention. Bird et al. Science, 1988, 242:423-426. Huston et al., Proc. Natl. Acad. Sci. USA, 1988, 85:5879-5883.

The antibodies or antigen-binding portions thereof of the present invention may be monospecific, bi-specific or multispecific. Multispecific or bi-specific antibodies or fragments thereof may be specific for different epitopes of one target carbohydrate (e.g., Globo H) or may contain antigen-binding domains specific for more than one target carbohydrate (e.g., antigen-binding domains specific for Globo H, SSEA-3 and SSEA-4). In one embodiment, a multispecific antibody or antigen-binding portion thereof comprises at least two different variable domains, wherein each variable domain is capable of specifically binding to a separate carbohydrate antigen or to a different epitope on the same carbohydrate antigen. Tutt et al., 1991, J. Immunol. 147:60-69. Kufer et al., 2004, Trends Biotechnol. 22:238-244. The present antibodies can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity.

All antibody isotypes are encompassed by the present invention, including IgG (e.g., IgG1, IgG2, IgG3, IgG4), IgM, IgA (IgA1, IgA2), IgD or IgE (all classes and sub-classes are encompassed by the present invention). The antibodies or antigen-binding portions thereof may be mammalian (e.g., mouse, human) antibodies or antigen-binding portions thereof. The light chains of the antibody may be of kappa or lambda type.

The variable regions of the present antibodies or antigen-binding portions thereof can be from a non-human or human source. The framework of the present antibodies or antigen-binding portions thereof can be human, humanized, non-human (e.g., a murine framework modified to decrease antigenicity in humans), or a synthetic framework (e.g., a consensus sequence).

In one embodiment, the present antibodies, or antigen-binding portions thereof, comprise at least one heavy chain variable region and/or at least one light chain variable region.

The present antibodies or antigen-binding portions thereof specifically bind to Globo H with a dissociation constant ($K_D$) of less than about 10E-7 M, less than about 10E-8 M, less than about 10E-9 M, less than about 10E-10 M, less than about 10E-11 M, or less than about 10E-12 M. In one embodiment, the antibody or the antibody binding portion thereof has a dissociation constant ($K_D$) of 1~10× 10E-9 or less. In another embodiment, the Kd is determined by surface plasmon resonance.

Antibodies with a variable heavy chain region and a variable light chain region that are at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% homologous to the variable heavy chain region and variable light chain region of the antibody produced by clone 2C2, and can also bind to a carbohydrate antigen (e.g. Globo H). Homology can be present at either the amino acid or nucleotide sequence level.

In some embodiments, the antibodies or antigen-binding portions thereof include, for example, the variable heavy chains and/or variable light chains of the antibodies produced by hybridoma 2C2, hybridoma 3D7, hybridoma 7A11, hybridoma 2F8 and hybridoma 1E1, are shown in Table 1.

In related embodiments, the antibodies or antigen-binding portions thereof include, for example, the CDRs of the variable heavy chains and/or the CDRs of the variable light chains of the antibodies produced from hybridoma 2C2, hybridoma 3D7, hybridoma 7A11, hybridoma 2F8 and hybridoma 1E1. The CDRs and frameworks of the variable heavy chains and the variable light chains from these hybridoma clones are shown in Table 1.

TABLE 1

Sequense Listing: SEQ ID NO. 1-90

| Hybridoma Clones | Chain Region | Sequence | SEQ ID No. |
|---|---|---|---|
| 2C2 | Heavy Chain Variable Region (Vh) | Nucleic acid Sequence<br>TCTGGCCCTGGGATATTGCAGCCCTCCC<br>AGACCCTCAGTCTGACTTGTTCTTTCTCT<br>GGATTTTCACTGTACACTTTTGATATGG<br>GTGTAGGCTGGATTCGTCAGCCTTCAGG<br>GAAGGGTCTGGAGTGGCTGGCACACAT<br>TTGGTGGGATGATGATAAGTACTATAAC<br>CCAGCCCTGAAGAGTCGGCTCACAGTCT<br>CCAAGGATACCTCCAAAAACCAGGTCTT<br>CCTCAAGATCCCCAATGTGGACACTGCA<br>GATAGTGCCACATACTACTGTGCTCGAG<br>TAAGGGGCCTCCATGATTATTACTACTG<br>GTTTGCTTACTGGGGCCAAGGGACTCTG<br>GTCACTGTCTCT | 1 |
| 2C2 | Light Chain Variable Region (VL) | Nucleic acid Sequence<br>GCATCTCCAGGGGAGAAGGTCACAATG<br>ACTTGCAGGGCCAGTTCAAGTGTAAGTT<br>ACATGCACTGGTACCAGCAGAAGCCAG<br>GATCCTCCCCCAAACCCTGGATTTATGC<br>CACATCCAACCTGGCGTCTGGAGTCCCT<br>GCTCGCTTCAGTGGCAGTGGGTCTGGGA<br>CCTCTTACTCTCTCACAATCAGCAGAGT<br>GGAGGCTGAAGATGCTGCCACTTATTTC<br>TGCCAGCAGTGGAGTCGAAACCCATTC<br>ACGTTCGGCTCGGGGACAAAGTTGGAA<br>ATAAGA | 2 |
| 2C2 | Heavy Chain Variable Region (Vh) | Amino Acid Sequence<br>SGPG ILQPSQTLSL TCSFSGFSLY<br>TFDMGVGWIR QPSGKGLEWL<br>AHIWWDDDKY YNPALKSRLT<br>VSKDTSKNQV FLKIPNVDTA<br>DSATYYCARV RGLHDYYYWF<br>AYWGQGTLVT VS | 3 |
| 2C2 | Light Chain (VL) | Amino Acid Sequence<br>ASPGEKVT MTCRASSSVS<br>YMHWYQQKPG SSPKPWIYAT<br>SNLASGVPAR FSGSGSGTSY<br>SLTISRVEAE DAATYFCQQW<br>SRNPFTFGSG TKLEIR | 4 |
| 2C2 | Heavy Chain CDR1 | Amino Acid Sequence<br>YTFDMGVG | 5 |
| 2C2 | Heavy Chain CDR2 | Amino Acid Sequence<br>HIWWDDDKYYNPALKS | 6 |
| 2C2 | Heavy Chain CDR3 | Amino Acid Sequence<br>VRGLHDYYYWFAY | 7 |
| 2C2 | Light Chain CDR1 | Amino Acid Sequence<br>RASSSVSYMH | 8 |
| 2C2 | Light Chain CDR2 | Amino Acid Sequence<br>ATSNLAS | 9 |
| 2C2 | Light Chain CDR3 | Amino Acid Sequence<br>QQWSRNPFT | 10 |

TABLE 1 -continued

Sequense Listing: SEQ ID NO. 1-90

| Hybridoma Clones | Chain Region | Sequence | SEQ ID No. |
|---|---|---|---|
| 2C2 | Heavy Chain Framework 2 | Amino Acid Sequence WIRQPSGKGLEWLA | 11 |
| 2C2 | Light Chain Framework 2 | Amino Acid Sequence WYQQKPGSSPKPWIY | 12 |
| 3D7 | Heavy Chain Variable Region (Vh) | Amino Acid Sequence SGPGILQPSQTLSLTCSFSGFSLYTFDMGV GWIRQPSGKGLEWLAHIWWDDDKYYNP ALKSRLTVSKDTSKNQVFLKIPNVDTADS ATYYCARVRGLHDYYYWFAYWGQGTL VTVS | 13 |
| 3D7 | Light Chain Variable Region (VL) | Amino Acid Sequence ASPGEKVTMTCRASSSVSYMHWYQQKPG SSPKPWIYATSNLASGVPARFSGSGSGTSY SLTISRVEAEDAATYFCQQWSRNPFTFGS GTKLEIR | 14 |
| 3D7 | Heavy Chain CDR1 | Amino Acid Sequence YTFDMGVG | 15 |
| 3D7 | Heavy Chain CDR2 | Amino Acid Sequence HIWWDDDKYYNPALKS | 16 |
| 3D7 | Heavy Chain CDR3 | Amino Acid Sequence VRGLHDYYYWFAY | 17 |
| 3D7 | Light Chain CDR1 | Amino Acid Sequence RASSSVSYMH | 18 |
| 3D7 | Light Chain CDR2 | Amino Acid Sequence ATSNLAS | 19 |
| 3D7 | Light Chain CDR3 | Amino Acid Sequence QQWSRNPFT | 20 |
| 7A11 | Heavy Chain Variable Region (Vh) | Amino Acid Sequence SGPGILQPSQTLSLTCSFSGFSLYTFDMGV GWIRQPSGKGLEWLAQIWWDDDKYYNP GLKSRLTISKDTSKNQVFLKIPNVDTADSA TYYCARIRGLRDYYYWFAYWGQGTLVT VS | 21 |
| 7A11 | Light Chain Variable Region (VL) | Amino Acid Sequence ASPGEKVTMTCRASSSVSYMHWYQQKPG SSPKPWIYATSNLASGVPARFSGSGSGTSY SLTISRVEAEDAATYFCQQWSRNPFTFGS GTKLEIR | 22 |
| 7A11 | Heavy Chain CDR1 | Amino Acid Sequence YTFDMGVG | 23 |
| 7A11 | Heavy Chain CDR2 | Amino Acid Sequence QIWWDDDKYYNPGLKS | 24 |
| 7A11 | Heavy Chain CDR3 | Amino Acid Sequence IRGLRDYYYWFAY | 25 |

TABLE 1 -continued

Sequense Listing: SEQ ID NO. 1-90

| Hybridoma Clones | Chain Region | Sequence | SEQ ID No. |
|---|---|---|---|
| 7A11 | Light Chain CDR1 | Amino Acid Sequence<br>RASSSVSYMH | 26 |
| 7A11 | Light Chain CDR2 | Amino Acid Sequence<br>ATSNLAS | 27 |
| 7A11 | Light Chain CDR3 | Amino Acid Sequence<br>QQWSRNPFT | 28 |
| 2F8 | Heavy Chain Variable Region (Vh) | Amino Acid Sequence<br>SGPGILQPSQTLSLTCSFSGFSLSTFGLGVG<br>WIRQPSGKGLEWLAHIWWDDDKSYNPAL<br>KSRLTISKDTSKNQVFLMIANVDTADTAT<br>YYCARIGPKWSNYYYYCDYWGQGTTLT<br>VS | 29 |
| 2F8 | Light Chain Variable Region (VL) | Amino Acid Sequence<br>ASPGEKVTMTCRASSSVSYMHWYQQKPG<br>SSPKPYIYATSNLSSGVPARFSGSGSGTSY<br>SLTISRVEAEDAATYYCQQWSSNPFTFGS<br>GTKLEIK | 30 |
| 2F8 | Heavy Chain CDR1 | Amino Acid Sequence<br>STFGLGVG | 31 |
| 2F8 | Heavy Chain CDR2 | Amino Acid Sequence<br>HIWWDDDKSYNPALKS | 32 |
| 2F8 | Heavy Chain CDR3 | Amino Acid Sequence<br>IGPKWSNYYYYCDY | 33 |
| 2F8 | Light Chain CDR1 | Amino Acid Sequence<br>RASSSVSYMH | 34 |
| 2F8 | Light Chain CDR2 | Amino Acid Sequence<br>ATSNLSS | 35 |
| 2F8 | Light Chain CDR3 | Amino Acid Sequence<br>QQWSSNPFT | 36 |
| 1E1 | Heavy Chain Variable Region (Vh) | Amino Acid Sequence<br>SGPGILQPSQTLSLTCSFSGFSLSTFGLGVG<br>WIRQPSGKGLEWLAHIWWDDDKSYNPAL<br>KSQLTISKDTSKNQVLLKIANVDTADTAT<br>YYCARIGPKWSNYYYYCDYWGQGTTLT<br>VS | 37 |
| 1E1 | Light Chain Variable Region (VL) | Amino Acid Sequence<br>ASPGEKVTMTCRASSSVSYMHWYQQKPG<br>SSPKPYIYATSNLSSGVPARFSGSGSGTSY<br>SLTISRVEAEDAATYYCQQWSSNPFTFGS<br>GTKLEIK | 38 |
| 1E1 | Heavy Chain CDR1 | Amino Acid Sequence<br>STFGLGVG | 39 |
| 1E1 | Heavy Chain CDR2 | Amino Acid Sequence<br>HIWWDDDKSYNPALKS | 40 |
| 1E1 | Heavy Chain CDR3 | Amino Acid Sequence<br>IGPKWSNYYYYCDY | 41 |

TABLE 1 -continued

Sequense Listing: SEQ ID NO. 1-90

| Hybridoma Clones | Chain Region | Sequence | SEQ ID No. |
|---|---|---|---|
| 1E1 | Light Chain CDR1 | Amino Acid Sequence<br>RAS S SVSYMH | 42 |
| 1E1 | Light Chain CDR2 | Amino Acid Sequence<br>ATSNLSS | 43 |
| 1E1 | Light Chain CDR3 | Amino Acid Sequence<br>QQWSSNPFT | 44 |
| 2C2 | Heavy Chain CDR1 | Nucleic Acid Sequence<br>TACACTTTTGATATGGGTGTAGGC | 45 |
| 2C2 | Heavy Chain CDR2 | Nucleic Acid Sequence<br>CACATTTGGTGGGATGATGATAAGTACT<br>ATAACCCAGCCCTGAAGAGT | 46 |
| 2C2 | Heavy Chain CDR3 | Nucleic Acid Sequence<br>GTAAGGGGCCTCCATGATTATTACTACT<br>GGTTTTGCTTAC | 47 |
| 2C2 | Light Chain CDR1 | Nucleic Acid Sequence<br>AGGGCCAGTTCAAGTGTAAGTTACATGC<br>AC | 48 |
| 2C2 | Light Chain CDR2 | Nucleic Acid Sequence<br>GCCACATCCAACCTGGCGTCT | 49 |
| 2C2 | Light Chain CDR3 | Nucleic Acid Sequence<br>CAGCAGTGGAGTCGAAACCCATTCACG | 50 |
| 3D7 | Heavy Chain Variable Region (Vh) | Nucleic Acid Sequence<br>TCTGGCCCTGGGATATTGCAGCCCTCCC<br>AGACCCTCAGTCTGACTTGTTCTTTCTCT<br>GGATTTTCACTGTACACTTTTGATATGG<br>GTGTAGGCTGGATTCGTCAGCCTTCAGG<br>GAAGGGTCTGGAGTGGCTGGCACACAT<br>TTGGTGGGATGATGATAAGTACTATAAC<br>CCAGCCCTGAAGAGTCGGCTCACAGTCT<br>CCAAGGATACCTCCAAAAACCAGGTCTT<br>CCTCAAGATCCCCAATGTGGACACTGCA<br>GATAGTGCCACATACTACTGTGCTCGAG<br>TAAGGGGCCTCCATGATTATTACTACTG<br>GTTTGCTTACTGGGGCCAAGGGACTCTG<br>GTCACTGTCTCT | 51 |
| 3D7 | Light Chain Variable Region (VL) | Nucleic Acid Sequence<br>GCATCTCCAGGGGAGAAGGTCACAATG<br>ACTTGCAGGGCCAGTTCAAGTGTAAGTT<br>ACATGCACTGGTACCAGCAGAAGCCAG<br>GATCCTCCCCCAAACCCTGGATTTATGC<br>CACATCCAACCTGGCGTCTGGAGTCCCT<br>GCTCGCTTCAGTGGCAGTGGGTCTGGGA<br>CCTCTTACTCTCTCACAATCAGCAGAGT<br>GGAGGCTGAAGATGCTGCCACTTATTTC<br>TGCCAGCAGTGGAGTCGAAACCCATTC<br>ACGTTCGGCTCGGGGACAAAGTTGGAA<br>ATAAGA | 52 |
| 3D7 | Heavy Chain CDR1 | Nucleic Acid Sequence<br>TACACTTTTGATATGGGTGTAGGC | 53 |
| 3D7 | Heavy Chain CDR2 | Nucleic Acid Sequence<br>CACATTTGGTGGGATGATGATAAGTACT<br>ATAACCCAGCCCTGAAGAGT | 54 |

TABLE 1 -continued

Sequense Listing: SEQ ID NO. 1-90

| Hybridoma Clones | Chain Region | Sequence | SEQ ID No. |
|---|---|---|---|
| 3D7 | Heavy Chain CDR3 | Nucleic Acid Sequence<br>GTAAGGGGCCTCCATGATTATTACTACT<br>GGTTTGCTTAC | 55 |
| 3D7 | Light Chain CDR1 | Nucleic Acid Sequence<br>AGGGCCAGTTCAAGTGTAAGTTACATGC<br>AC | 56 |
| 3D7 | Light Chain CDR2 | Nucleic Acid Sequence<br>GCCACATCCAACCTGGCGTCT | 57 |
| 3D7 | Light Chain CDR3 | Nucleic Acid Sequence<br>CAGCAGTGGAGTCGAAACCCATTCACG | 58 |
| 7A11 | Heavy Chain Variable Region (Vh) | Nucleic Acid Sequence<br>TCTGGCCCTGGGATATTGCAGCCCTCCC<br>AGACCCTCAGTCTGACTTGTTCTTTCTCT<br>GGATTTTCACTGTACACTTTTGATATGG<br>GTGTAGGCTGGATTCGTCAGCCTTCAGG<br>GAAGGGTCTGGAGTGGCTGGCACAAAT<br>TTGGTGGGATGATGATAAGTACTATAAC<br>CCAGGCCTGAAGAGTCGGCTCACAATCT<br>CCAAGGATACCTCCAAAAACCAGGTAT<br>TCCTCAAGATCCCCAATGTGGACACTGC<br>AGATAGTGCCACATACTACTGTGCTCGA<br>ATAAGGGGCCTCCGTGATTATTACTACT<br>GGTTTGCTTACTGGGGCCAAGGGACTCT<br>GGTCACTGTCTCT | 59 |
| 7A11 | Light Chain Variable Region (VL) | Nucleic Acid Sequence<br>GCATCTCCAGGGGAGAAGGTCACAATG<br>ACTTGCAGGGCCAGCTCAAGTGTAAGTT<br>ACATGCACTGGTACCAGCAGAAGCCAG<br>GATCCTCCCCCAAACCCTGGATTTATGC<br>CACATCCAACCTGGCTTCTGGAGTCCCT<br>GCTCGCTTCAGTGGCAGTGGGTCTGGGA<br>CCTCTTACTCTCTCACAATCAGCAGAGT<br>GGAGGCTGAAGATGCTGCCACTTATTTC<br>TGCCAGCAGTGGAGTCGAAACCCATTC<br>ACGTTCGGCTCGGGGACAAAGTTGGAA<br>ATAAGA | 60 |
| 7A11 | Heavy Chain CDR1 | Nucleic Acid Sequence<br>TACACTTTTGATATGGGTGTAGGC | 61 |
| 7A11 | Heavy Chain CDR2 | Nucleic Acid Sequence<br>CAAATTTGGTGGGATGATGATAAGTACT<br>ATAACCCAGGCCTGAAGAGT | 62 |
| 7A11 | Heavy Chain CDR3 | Nucleic Acid Sequence<br>ATAAGGGGCCTCCGTGATTATTACTACT<br>GGTTTGCTTAC | 63 |
| 7A11 | Light Chain CDR1 | Nucleic Acid Sequence<br>AGGGCCAGCTCAAGTGTAAGTTACATG<br>CAC | 64 |
| 7A11 | Light Chain CDR2 | Nucleic Acid Sequence<br>GCCACATCCAACCTGGCTTCT | 65 |
| 7A11 | Light Chain CDR3 | Nucleic Acid Sequence<br>CAGCAGTGGAGTCGAAACCCATTCACG | 66 |
| 2F8 | Heavy Chain Variable Region (Vh) | Nucleic Acid Sequence<br>TCTGGCCCTGGGATATTGCAGCCCTCCC<br>AGACCCTCAGTCTGACTTGTTCTTTCTCT<br>GGGTTTTCGCTGAGCACTTTTGGTTTGG<br>GTGTAGGCTGGATTCGTCAGCCTTCAGG | 67 |

TABLE 1 -continued

Sequense Listing: SEQ ID NO. 1-90

| Hybridoma Clones | Chain Region | Sequence | SEQ ID No. |
|---|---|---|---|
| | | GAAGGGTCTGGAGTGGCTGGCACACAT TTGGTGGGATGATGATAAGTCCTATAAC CCAGCCCTGAAGAGTCGGCTCACAATCT CCAAGGATACCTCCAAAAACCAGGTCTT CCTCATGATCGCCAATGTGGACACTGCA GATACTGCCACATACTACTGTGCTCGAA TAGGCCCGAAATGGAGCAACTACTACT ACTACTGTGACTACTGGGGCCAAGGCA CCACTCTCACAGTCTCC | |
| 2F8 | Light Chain Variable Region (VL) | Nucleic Acid Sequence GCATCTCCAGGGGAGAAGGTCACAATG ACTTGCAGGGCCAGCTCAAGTGTTAGTT ACATGCACTGGTACCAGCAGAAGCCAG GATCCTCCCCCAAACCCTACATTTATGC CACATCCAACCTGTCTTCTGGAGTCCCT GCTCGCTTCAGTGGCAGTGGGTCTGGGA CCTCTTACTCTCTCACAATCAGCAGAGT GGAGGCTGAAGATGCTGCCACTTATTAC TGCCAGCAGTGGAGTAGTAACCCCTTCA CGTTCGGCTCGGGGACAAAGTTGGAAA TAAAA | 68 |
| 2F8 | Heavy Chain CDR1 | Nucleic Acid Sequence AGCACTTTTGGTTTGGGTGTAGGC | 69 |
| 2F8 | Heavy Chain CDR2 | Nucleic Acid Sequence CACATTTGGTGGGATGATGATAAGTCCT ATAACCCAGCCCTGAAGAGT | 70 |
| 2F8 | Heavy Chain CDR3 | Nucleic Acid Sequence ATAGGCCCGAAATGGAGCAACTACTAC TACTACTGTGACTAC | 71 |
| 2F8 | Light Chain CDR1 | Nucleic Acid Sequence AGGGCCAGCTCAAGTGTTAGTTACATGC AC | 72 |
| 2F8 | Light Chain CDR2 | Nucleic Acid Sequence GCCACATCCAACCTGTCTTCT | 73 |
| 2F8 | Light Chain CDR3 | Nucleic Acid Sequence CAGCAGTGGAGTAGTAACCCCTTCACG | 74 |
| 1E1 | Heavy Chain Variable Region (Vh) | Nucleic Acid Sequence TCTGGCCCTGGGATATTGCAGCCCTCCC AGACCCTCAGTCTGACTTGTTCTTTCTCT GGGTTTTCGCTGAGCACTTTTGGTTTGG GTGTAGGCTGGATTCGTCAGCCTTCAGG GAAGGGTCTGGAGTGGCTGGCACACAT TTGGTGGGATGATGATAAGTCCTATAAC CCAGCCCTGAAGAGTCAGCTCACAATCT CCAAGGATACCTCCAAAAACCAGGTAC TCCTCAAGATCGCCAATGTGGACACTGC AGATACTGCCACATACTACTGTGCTCGA ATAGGCCCGAAATGGAGCAACTACTAC TACTACTGTGACTACTGGGGCCAAGGCA CCACTCTCACAGTCTCC | 75 |
| 1E1 | Light Chain Variable Region (VL) | Nucleic Acid Sequence GCATCTCCAGGGGAGAAGGTCACAAT GACTTGCAGGGCCAGCTCAAGTGTTA GTTACATGCACTGGTACCAGCAGAAG CCAGGATCCTCCCCCAAACCCTACAT TTATGCCACATCCAACCTGTCTTCTGG AGTCCCTGCTCGCTTCAGTGGCAGTG GGTCTGGGACCTCTTACTCTCTCACAA TCAGCAGAGTGGAGGCTGAAGATGCT GCCACTTATTACTGCCAGCAGTGGAG TAGTAACCCCTTCACGTTCGGCTCGG GGACAAAGTTGGAAATAAAA | 76 |

TABLE 1 -continued

Sequence Listing: SEQ ID NO. 1-90

| Hybridoma Clones | Chain Region | Sequence | SEQ ID No. |
|---|---|---|---|
| 1E1 | Heavy Chain CDR1 | Nucleic Acid Sequence<br>AGCACTTTTGGTTTGGGTGTAGGC | 77 |
| 1E1 | Heavy Chain CDR2 | Nucleic Acid Sequence<br>CACATTTGGTGGGATGATGATAAGTCCT<br>ATAACCCAGCCCTGAAGAGT | 78 |
| 1E1 | Heavy Chain CDR3 | Nucleic Acid Sequence<br>ATAGGCCCGAAATGGAGCAACTACTAC<br>TACTACTGTGACTAC | 79 |
| 1E1 | Light Chain CDR1 | Nucleic Acid Sequence<br>AGGGCCAGCTCAAGTGTTAGTTACATGC<br>AC | 80 |
| 1E1 | Light Chain CDR2 | Nucleic Acid Sequence<br>GCCACATCCAACCTGTCTTCT | 81 |
| 1E1 | Light Chain CDR3 | Nucleic Acid Sequence<br>CAGCAGTGGAGTAGTAACCCCTTCACG | 82 |
| 2C2 | Heavy Chain Frame work 1 | Amino Acid Sequence<br>SGPGILQPSQTLSLTCSFSGFSL | 83 |
| 2C2 | Light Chain Frame work 1 | Amino Acid Sequence<br>ASPGEKVTMTC | 84 |
| 2C2 | Heavy Chain Frame work 3 | Amino Acid Sequence<br>RLTVSKDTSKNQVFLKIPNVDTA<br>DSATYYCAR | 85 |
| 2C2 | Light Chain Frame work 3 | Amino Acid Sequence<br>GVPARFSGSGSGTSYSLTISRVEAE<br>DAATYFC | 86 |
| 2C2 | Heavy Chain Frame work 1 | Amino Acid Sequence of Humanized Antibody<br>SGPTLVKPTQTLTLTCTFSGFSL | 87 |
| 2C2 | Light Chain Frame work 1 | Amino Acid Sequence of Humanized Antibody<br>LSPGERATLSC | 88 |
| 2C2 | Heavy Chain Frame work 3 | Amino Acid Sequence of Humanized Antibody<br>RLTISKDTSKNQVVLTMTNMDPVDTATY<br>YCAR | 89 |
| 2C2 | Light Chain Frame work 3 | Amino Acid Sequence of Humanized Antibody<br>GVPSRFSGSGSGTDFTFTISSLQPEDIATYY<br>C | 90 |

The invention also encompasses a nucleic acid encoding the present antibody or antigen-binding portion thereof that specifically binds to a carbohydrate antigen. In one embodiment, the carbohydrate antigen is Globo H. In another embodiment, the carbohydrate antigen is SSEA-3. In yet another embodiment, the carbohydrate antigen is SSEA-4. The nucleic acid may be expressed in a cell to produce the present antibody or antigen-binding portion thereof.

In certain embodiments, the antibodies or antigen-binding portions thereof include a variable heavy chain region comprising an amino acid sequence that is at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% homologous to any of the following:
  a) SEQ ID NO: 3 (Hybridoma 2C2);
  b) SEQ ID NO: 13 (Hybridoma 3D7);
  c) SEQ ID NO: 21 (Hybridoma 7A11);
  d) SEQ ID NO: 29 (Hybridoma 2F8); or
  e) SEQ ID NO: 37 (Hybridoma 1E1).

In certain embodiments, the antibodies or antigen-binding portions thereof include a variable light chain region comprising an amino acid sequence that is at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% homologous to any of the following:
  a) SEQ ID NO: 4 (Hybridoma 2C2);
  b) SEQ ID NO: 14 (Hybridoma 3D7);
  c) SEQ ID NO: 22 (Hybridoma 7A11);
  d) SEQ ID NO: 30 (Hybridoma 2F8); or
  e) SEQ ID NO: 38 (Hybridoma 1E1).

In certain embodiments, a variable heavy chain region of the antibodies or antigen-binding portions thereof comprises an amino acid sequence that is at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% homologous to SEQ ID NO: 3, and a variable light chain region of the antibodies or antigen-binding portions thereof comprises an amino acid sequence that is at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% homologous to SEQ ID NO: 4.

In certain embodiments, a variable heavy chain region of the antibodies or antigen-binding portions thereof comprises an amino acid sequence that is at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% homologous to SEQ ID NO: 13, and a variable light chain region of the antibodies or antigen-binding portions thereof comprises an amino acid sequence that is at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% homologous to SEQ ID NO: 14.

In certain embodiments, a variable heavy chain region of the antibodies or antigen-binding portions thereof comprises an amino acid sequence that is at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% homologous to SEQ ID NO: 21, and a variable light chain region of the antibodies or antigen-binding portions thereof comprises an amino acid sequence that is at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% homologous to SEQ ID NO: 22.

In certain embodiments, a variable heavy chain region of the antibodies or antigen-binding portions thereof comprises an amino acid sequence that is at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% homologous to SEQ ID NO: 29, and a variable light chain region of the antibodies or antigen-binding portions thereof comprises an amino acid sequence that is at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% homologous to SEQ ID NO: 30.

In certain embodiments, a variable heavy chain region of the antibodies or antigen-binding portions thereof comprises an amino acid sequence that is at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% homologous to SEQ ID NO: 37, and a variable light chain region of the antibodies or antigen-binding portions thereof comprises an amino acid sequence that is at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% homologous to SEQ ID NO: 38.

A variable heavy chain region of the antibodies or antigen-binding portions thereof can comprise one, two three or more CDRs comprise amino acid sequences that are at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to any of the following:
  a) CDRs of the variable heavy chain region of an antibody produced by hybridoma 2C2 (SEQ ID NOs: 5, 6 and 7);
  b) CDRs of the variable heavy chain region of an antibody produced by hybridoma 3D7 (SEQ ID NOs: 15, 16 and 17);
  c) CDRs of the variable heavy chain region of an antibody produced by hybridoma 7A11 (SEQ ID NOs: 23, 24 and 25);
  d) CDRs of the variable heavy chain region of an antibody produced by hybridoma 2F8 (SEQ ID NOs: 31, 32 and 33); or
  e) CDRs of the variable heavy chain region of an antibody produced by hybridoma 1E1 (SEQ ID No: 39, 40 and 41).

A variable light chain region of the antibodies or antigen-binding portions thereof can comprise one, two three or more CDRs comprise amino acid sequences that are at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to any one of the following:
  a) CDRs of the variable light chain region of an antibody produced by hybridoma 2C2 (SEQ ID NOs: 8, 9 and 10);
  b) CDRs of the variable light chain region of an antibody produced by hybridoma 3D7 (SEQ ID NOs: 18, 19 and 20);
  c) CDRs of the variable light chain region of an antibody produced by hybridoma 7A11 (SEQ ID NOs: 26, 27 and 28);
  d) CDRs of the variable light chain region of an antibody produced by hybridoma 2F8 (SEQ ID NOs: 34, 35 and 36); or
  e) CDRs of the variable light chain region of an antibody produced by hybridoma 1E1 (SEQ ID NOs: 42, 43 and 44).

A variable heavy chain region of the antibodies or antigen-binding portions thereof can comprise one, two three or more CDRs comprise amino acid sequences that are at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to CDRs of the variable heavy chain region of an antibody produced by hybridoma 2C2 (SEQ ID NOs: 5, 6, 7) or CDRs of the variable heavy chain region of an antibody produced by hybridoma 3D7 (SEQ ID NOs: 15, 16 and 17), and a variable light chain region of the antibodies or antigen-binding portions thereof can comprise one, two three or more CDRs comprise amino acid sequences that are at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to CDRs of the variable light chain region of an antibody produced by hybridoma 2C2 (SEQ ID NOs: 8, 9 and 10) or CDRs of the variable light chain region of an antibody produced by hybridoma 3D7 (SEQ ID NOs: 18, 19 and 20).

In one embodiment, the antibodies or antigen-binding portions thereof further comprises a framework at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to SEQ ID NO: 83 (Heavy Chain Framework1 of 2C2 antibody) or SEQ ID NO: 87 (Heavy Chain Framework 1 of Humanized 2C2 Antibody, see Table 1), wherein the framework is between a leader sequence and CDR1 of a variable heavy chain region of the antibody produced by hybridoma 2C2. In another embodiment, the antibodies or antigen-binding portions thereof further comprises a framework at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to SEQ ID NO: 84 (Light Chain Framework 1 of 2C2 antibody) or SEQ ID NO:88 (Light Chain Framework 1 of Humanized 2C2 Antibody, see Table 1) and said framework is between a leader sequence and CDR1 of the variable light chain region of the antibody produced by hybridoma 2C2.

In one embodiment, the antibodies or antigen-binding portions thereof further comprises a framework between CDR1 and CDR2 of the variable heavy chain region of the antibody produced by hybridoma 2C2, wherein the framework is at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to SEQ ID NO: 11 (Heavy Chain Framework 2 in Table 1). In an exemplary embodiment, the framework between CDR1 and CDR2 of a variable heavy chain region having amino acid sequence about 80% to about 100% homologous to SEQ ID NO: 11, contains glycine at position 9. The position of the amino acid of SEQ ID NO: 11 is illustrated below:

```
Amino Acid     W*  I  R  Q  P  S  GKG  L  E   W   L   A**
Position No.   1   2  3  4  5  6  789  10 11  12  13  14
```
*The amino acid at position 1 of FW2 (W) is the residue adjacent to CDR 1.
**The amino acid at position 14 of FW2 (A) is the residue adjacent to CDR2.

In another embodiment, the antibodies or antigen-binding portions thereof further comprises a framework between CDR1 and CDR2 of the variable light chain region of an antibody produced by hybridoma 2C2, wherein the framework is at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to SEQ ID NO: 12 (Light Chain Framework 2 in Table 1). In an exemplary embodiment, the framework between CDR1 and CDR2 of a variable light chain region of the antibody produced by hybridoma 2C2 contains proline at position 12. In another exemplary embodiment, the framework between CDR1 and CDR2 of a variable light chain region of the antibody produced by hybridoma 2C2 contains tryptophan at position 13. In yet another exemplary embodiment, the framework between CDR1 and CDR2 of a variable light chain region of the antibody produced by hybridoma 2C2 contains proline at position 12 and tryptophan at position 13. The position of the amino acid of SEQ ID NO: 12 is illustrated below:

```
Amino Acid     W*  Y  Q Q K P G S S  P   K   P   W   I   Y**
Position No.   1   2  3 4 5 6 7 8 9  10  11  12  13  14  15
```
*The amino acid at position 1 of FW2 (W) is the residue adjacent to CDR 1.
**The amino acid at position 15 of FW2 (Y) is the residue adjacent to CDR2.

In one embodiment, the antibodies or antigen-binding portions thereof further comprises a framework at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to SEQ ID NO: 85 (Heavy Chain Framework 3) or SEQ ID NO: 89 (Heavy Chain Framework 3 of Humanized Antibody, see in Table 1), wherein the framework is between CDR2 and CDR3 of a variable heavy chain region of the antibody produced by hybridoma 2C2. In another embodiment, the antibodies or antigen-binding portions thereof further comprises a framework at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to SEQ ID NO: 86 (Light Chain Framework 3) or SEQ ID NO: 90 (Light Chain Framework 3 of Humanized Antibody, see Table 1) and said framework is between CDR2 and CDR3 of a variable light chain region of the antibody produced by hybridoma 2C2.

A variable heavy chain region of the antibodies or antigen-binding portions thereof can comprise one, two three or more CDRs comprise amino acid sequences that are at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to CDRs of the variable heavy chain region of the antibody produced by hybridoma 7A11 (SEQ ID NOs: 23, 24 and 25), and a variable light chain region of the antibodies or antigen-binding portions thereof can comprise one, two three or more CDRs comprise amino acid sequences that are at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to CDRs of a variable light chain region of the antibody produced by hybridoma 7A11 (SEQ ID NOs: 26, 27 and 28).

A variable heavy chain region of the antibodies or antigen-binding portions thereof can comprise one, two three or more CDRs comprise amino acid sequences that are at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to CDRs of the variable heavy chain region of the antibody produced by hybridoma 2F8 (SEQ ID NOs: 31, 32 and 33) or CDRs of the variable heavy chain region of the antibody produced by hybridoma 1E1 (SEQ ID NOs: 39, 40 and 41), and a variable light chain region of the antibodies or antigen-binding portions thereof can comprise one, two three or more CDRs comprise amino acid sequences that are at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous to CDRs of the variable light chain region of the antibody produced by hybridoma 2F8 (SEQ ID NOs: 34, 35 and 36) or CDRs of the variable light chain region of the antibody produced by hybridoma 1E1 (SEQ ID NOs: 42, 43 and 44).

In certain embodiments, the variable regions corresponding to the variable regions in Table 1 have sequence variations. For example, a heavy chain variable region, in which 1, 2, 3, 4, 5, 6, 7 or 8 residues, or less than 40%, less than about 30%, about 25%, about 20%, about 15%, about 10%, about 9%, about 8%, about 7%, about 6%, about 5%, about 4%, about 3%, about 2% or about 1% amino acid residues substituted or deleted but retain essentially the same immunological properties including, but not limited to, binding to a carbohydrate antigen.

In certain embodiments, CDRs corresponding to the CDRs in Table 1 have sequence variations. For example, CDRs, in which 1, 2, 3, 4, 5, 6, 7 or 8 residues, or less than 20%, less than 30%, or less than about 40% of total residues in the CDR, are substituted or deleted can be present in an antibody (or antigen-binding portion thereof) that binds a carbohydrate antigen.

The antibodies or antigen-binding portions may be peptides. Such peptides can include variants, analogs, orthologs, homologs and derivatives of peptides, that exhibit a biological activity, e.g., binding of a carbohydrate antigen. The peptides may contain one or more analogs of an amino acid (including, for example, non-naturally occurring amino acids, amino acids which only occur naturally in an unrelated biological system, modified amino acids from mammalian systems etc.), peptides with substituted linkages, as well as other modifications known in the art.

Also within the scope of the invention are antibodies or antigen-binding portions thereof in which specific amino acids have been substituted, deleted or added. In an exemplary embodiment, these alternations do not have a substantial effect on the peptide's biological properties such as binding affinity. In another exemplary embodiment, antibodies may have amino acid substitutions in the framework region, such as to improve binding affinity of the antibody to the antigen. In yet another exemplary embodiment, a selected, small number of acceptor framework residues can be replaced by the corresponding donor amino acids. The donor framework can be a mature or germline human antibody framework sequence or a consensus sequence. Guidance concerning how to make phenotypically silent amino acid substitutions is provided in Bowie et al., Science, 247: 1306-1310 (1990). Cunningham et al., Science, 244: 1081-1085 (1989). Ausubel (ed.), Current Protocols in Molecular Biology, John Wiley and Sons, Inc. (1994). T. Maniatis, E. F. Fritsch and J. Sambrook, Molecular Cloning: A Laboratory Manual, Cold Spring Harbor laboratory, Cold Spring Harbor, N.Y. (1989). Pearson, Methods Mol. Biol. 243:307-31 (1994). Gonnet et al., Science 256:1443-45 (1992).

The antibody, or antigen-binding portion thereof, can be derivatized or linked to another functional molecule. For example, an antibody can be functionally linked (by chemical coupling, genetic fusion, noncovalent interaction, etc.) to one or more other molecular entities, such as another antibody, a detectable agent, a cytotoxic agent, a pharmaceutical agent, a protein or peptide that can mediate association with another molecule (such as a streptavidin core region or a polyhistidine tag), amino acid linkers, signal sequences, immunogenic carriers, or ligands useful in protein purification, such as glutathione-S-transferase, histidine tag, and staphylococcal protein A. One type of derivatized protein is produced by crosslinking two or more proteins (of the same type or of different types). Suitable crosslinkers include those that are heterobifunctional, having two distinct reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill. Useful detectable agents with which a protein can be derivatized (or labeled) include fluorescent compounds, various enzymes, prosthetic groups, luminescent materials, bioluminescent materials, and radioactive materials. Non-limiting, exemplary fluorescent detectable agents include fluorescein, fluorescein isothiocyanate, rhodamine, and, phycoerythrin. A protein or antibody can also be derivatized with detectable enzymes, such as alkaline phosphatase, horseradish peroxidase, beta-galactosidase, acetylcholinesterase, glucose oxidase and the like. A protein can also be derivatized with a prosthetic group (e.g., streptavidin/biotin and avidin/biotin).

Nucleic acids encoding a functionally active variant of the present antibody or antigen-binding portion thereof are also encompassed by the present invention. These nucleic acid molecules may hybridize with a nucleic acid encoding any of the present antibody or antigen-binding portion thereof under medium stringency, high stringency, or very high stringency conditions. Guidance for performing hybridization reactions can be found in Current Protocols in Molecular Biology, John Wiley & Sons, N.Y. 6.3.1-6.3.6, 1989, which is incorporated herein by reference. Specific hybridization conditions referred to herein are as follows: 1) medium stringency hybridization conditions: 6×SSC at about 45° C., followed by one or more washes in 0.2×SSC, 0.1% SDS at 60° C.; 2) high stringency hybridization conditions: 6×SSC at about 45° C., followed by one or more washes in 0.2×SSC, 0.1% SDS at 65° C.; and 3) very high stringency hybridization conditions: 0.5 M sodium phosphate, 7% SDS at 65° C., followed by one or more washes at 0.2×SSC, 1% SDS at 65° C.

A nucleic acid encoding the present antibody or antigen-binding portion thereof may be introduced into an expression vector that can be expressed in a suitable expression system, followed by isolation or purification of the expressed antibody or antigen-binding portion thereof. Optionally, a nucleic acid encoding the present antibody or antigen-binding portion thereof can be translated in a cell-free translation system. U.S. Pat. No. 4,816,567. Queen et al., Proc Natl Acad Sci USA, 86:10029-10033 (1989).

The present antibodies or antigen-binding portions thereof can be produced by host cells transformed with DNA encoding light and heavy chains (or portions thereof) of a desired antibody. Antibodies can be isolated and purified from these culture supernatants and/or cells using standard techniques. For example, a host cell may be transformed with DNA encoding the light chain, the heavy chain, or both, of an antibody. Recombinant DNA technology may also be used to remove some or all of the DNA encoding either or both of the light and heavy chains that is not necessary for binding, e.g., the constant region.

The present nucleic acids can be expressed in various suitable cells, including prokaryotic and eukaryotic cells, e.g., bacterial cells, (e.g., *E. coli*), yeast cells, plant cells, insect cells, and mammalian cells. A number of mammalian cell lines are known in the art and include immortalized cell lines available from the American Type Culture Collection (ATCC). Non-limiting examples of the cells include all cell lines of mammalian origin or mammalian-like characteristics, including but not limited to, parental cells, derivatives and/or engineered variants of monkey kidney cells (COS, e.g., COS-1, COS-7), HEK293, baby hamster kidney (BHK, e.g., BHK21), Chinese hamster ovary (CHO), NS0, PerC6, BSC-1, human hepatocellular carcinoma cells (e.g., Hep G2), SP2/0, HeLa, Madin-Darby bovine kidney (MDBK), myeloma and lymphoma cells. The engineered variants include, e.g., glycan profile modified and/or site-specific integration site derivatives.

The present invention also provides for cells comprising the nucleic acids described herein. The cells may be a hybridoma or transfectant, such as hybridoma designated as 2C2.

Alternatively, the present antibody or antigen-binding portion thereof can be synthesized by solid phase procedures well known in the art. Solid Phase Peptide Synthesis: A Practical Approach by E. Atherton and R. C. Sheppard, published by IRL at Oxford University Press (1989). Methods in Molecular Biology, Vol. 35: Peptide Synthesis Protocols (ed. M. W. Pennington and B. M. Dunn), chapter 7.

Solid Phase Peptide Synthesis, 2nd Ed., Pierce Chemical Co., Rockford, Ill. (1984). G. Barany and R. B. Merrifield, The Peptides: Analysis, Synthesis, Biology, editors E. Gross and J. Meienhofer, Vol. 1 and Vol. 2, Academic Press, New York, (1980), pp. 3-254. M. Bodansky, Principles of Peptide Synthesis, Springer-Verlag, Berlin (1984).

The present invention provides for methods for making an antibody or antigen-binding portion thereof that specifically binds to a carbohydrate antigen, (e.g., Globo H). For example, a non-human animal is immunized with a composition that includes a carbohydrate antigen (e.g., Globo H), and then a specific antibody is isolated from the animal. The method can further include evaluating binding of the antibody to a carbohydrate antigen.

Any of a variety of carbohydrate antigens, particularly Globo H, may be used in the practice of the present invention. Examples of carbohydrate antigens include, but are not limited to Globo antigens such as Globo H, stage-specific embryonic antigen 3 (SSEA-3) (also called Gb5), stage-specific embryonic antigen 4 (SSEA-4), Gb-4 and Gb-3, Lewis antigens such as sLe$^x$, Le$^x$, sLe$^a$, Le$^a$ and Le$^y$, polysaccharide antigens such as polysialic acid (PSA), sTn (c) and Tn(c), Thomsen-Friedenreich antigen (TF(c)), the ganglioside such as GD1, GD2, GD3, Fucosyl GM1, GM1, GM2, GM3, GD1α and GM2, sulfitide antigen such as 6Gal-HSO3-SiaLex and 6GluNAc-HSO3-SiaLex. Other carbohydrate antigens include, but are not limited to: α-Galactose, α-Man-6-phosphate, α-L-Rhamnose, α-GalNAc (Tn), α-NeuAc-OCH2C6H4-p-NHCOOCH2, Fucα1-2Galβ1-4GalNAcβ (H types3), NeuAcα2-8NeuAcα, (NeuAcα2-8)2 Polysialic acid, NeuAca2-6Galb, NeuAcb2-6Gala(STn), Gala1-3Galb1-4GlaNAcb (NeuAca2-8)3, GalNAcαa-3(Fucα1-2)Galβ (Blood Group A), Galα1-3 (Fucα1-2)Galβ (Blood Group B), 6Gal-HSO3-SiaLex, 6GluNAc-HSO3-SiaLex and a 2-6 sialylated diantennary N-glycans.

Figure 3A:
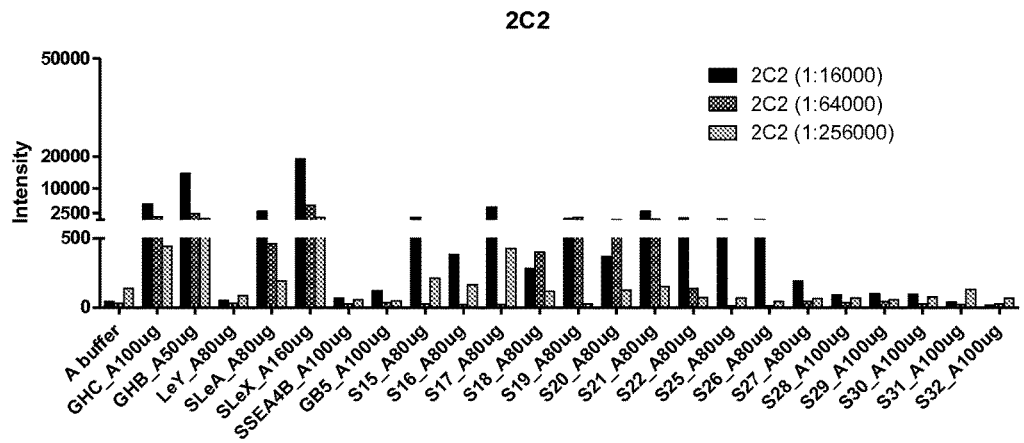
FIG. 3A-3F are bar graphs showing the binding affinity of Globo H-2C2 mAb (FIG. 3A), Globo H-7A11 mAb (FIG. 3B), Globo H-3D7 mAb (FIG. 3C), Globo H-2F8 mAb (FIG. 3D), Globo H-1E1 mAb (FIG. 3E) and Globo H-VK9 mAb (FIG. 3F) with various carbohydrate antigens.
Figure 3B:
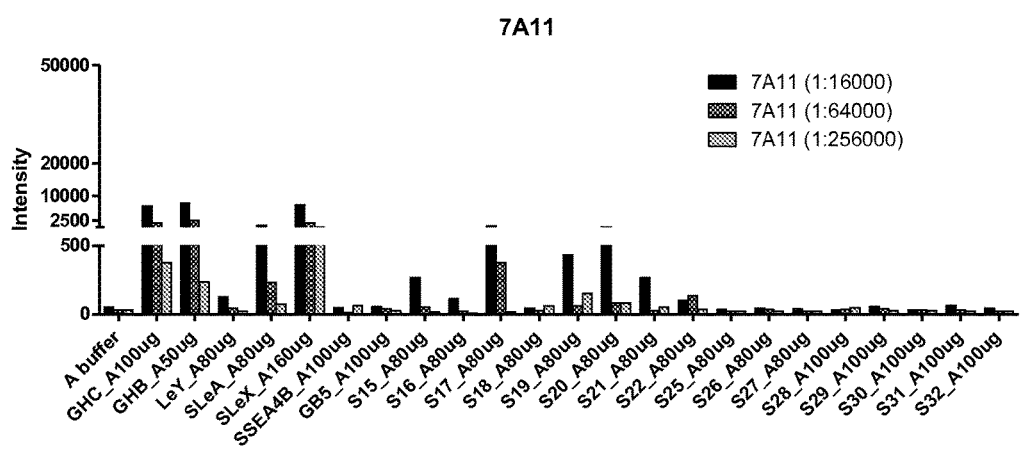

In one embodiment, the anti-Globo H antibody or the antigen binding portion thereof can cross react or bind with other carbohydrate antigens with high selectivity, as illustrated in FIG. 3A and FIG. 3B. Non limiting examples of the carbohydrate antigens are: SSEA-3, SSEA-4, Lewis antigens.

In one embodiment, the present invention provides for a method for making a hybridoma that expresses an antibody that specifically binds to a carbohydrate antigen (e.g., Globo H). The method contains the following steps: immunizing an animal with a composition that includes a carbohydrate antigen (e.g., Globo H); isolating splenocytes from the animal; generating hybridomas from the splenocytes; and selecting a hybridoma that produces an antibody that specifically binds to Globo H. Kohler and Milstein, Nature, 256: 495, 1975. Harlow, E. and Lane, D. Antibodies: A Laboratory Manual, Cold Spring Harbor Laboratory Press, Cold Spring Harbor, N.Y., 1988.

In one embodiment, carbohydrate antigen is used to immunize mice subcutaneously. One or more boosts may or may not be given. The titers of the antibodies in the plasma can be monitored by, e.g., ELISA (enzyme-linked immunosorbant assay) or flow cytometry. Mice with sufficient titers of anti-carbohydrate antigen antibodies are used for fusions. Mice may or may not be boosted with antigen 3 days before sacrifice and removal of the spleen. The mouse splenocytes are isolated and fused with PEG to a mouse myeloma cell line. The resulting hybridomas are then screened for the production of antigen-specific antibodies. Cells are plated, and then incubated in selective medium. Supernatants from individual wells are then screened by ELISA for human anti-carbohydrate antigen monoclonal antibodies. The antibody secreting hybridomas are replated, screened again, and if still positive for anti-carbohydrate antigen antibodies, can be subcloned by limiting dilution.

Adjuvants that may be used to increase the immunogenicity of one or more of the carbohydrate antigens. Non-limiting examples of adjuvants include aluminum phosphate, aluminum hydroxide, MF59 (4.3% w/v squalene, 0.5% w/v polysorbate 80 (Tween 80), 0.5% w/v sorbitan trioleate (Span 85)), CpG-containing nucleic acid, QS21 (saponin adjuvant), α-Galactosyl-ceramides or synthetic analogs thereof (e.g., C34, see U.S. Pat. No. 8,268,969), MPL (Monophosphoryl Lipid A), 3DMPL (3-O-deacylated MPL), extracts from Aquilla, ISCOMS (see, e.g., Sjolander et al. (1998) J. Leukocyte Biol. 64:713; WO90/03184; WO96/11711; WO 00/48630; WO98/36772; WO00/41720; WO06/134423 and WO07/026190), LT/CT mutants, poly (D,L-lactide-co-glycolide) (PLG) microparticles, Quil A, interleukins, Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dip-almitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/ Tween 80 emulsion.

The immunized animal can be any animal that is capable of producing recoverable antibodies when administered an immunogen, such as, but not limited to, rabbits, mice, rats, hamsters, goats, horses, monkeys, baboons and humans. In one aspect, the host is transgenic and produces human antibodies, e.g., a mouse expressing the human immunoglobulin gene segments. U.S. Pat. Nos. 8,236,311; 7,625,559 and 5,770,429, the disclosure of each of which is incorporated herein by reference in its entirety. Lonberg et al., Nature 368(6474): 856-859, 1994. Lonberg, N., Handbook of Experimental Pharmacology 113:49-101, 1994. Lonberg, N. and Huszar, D., Intern. Rev. Immunol., 13: 65-93, 1995. Harding, F. and Lonberg, N., Ann. N.Y. Acad. Sci., 764: 536-546, 1995.

After the host is immunized and the antibodies are produced, the antibodies are assayed to confirm that they are specific for the antigen of interest and to determine whether they exhibit any cross reactivity with other antigens. One method of conducting such assays is a sera screen assay as described in U.S. Patent Publication No. 2004/0126829. Anti-carbohydrate antigen antibodies can be characterized for binding to the carbohydrate by a variety of known techniques. For example, in an ELISA, microtiter plates are coated with the toxin or toxoid antigen in PBS, and then blocked with irrelevant proteins such as bovine serum albumin (BSA) diluted in PBS. Dilutions of plasma from toxin-immunized mice are added to each well and incubated. The plates are washed and then incubated with a secondary antibody conjugated to an enzyme (e.g., alkaline phosphatase). After washing, the plates are developed with the enzyme's substrate (e.g., ABTS), and analyzed at a specific OD. In other embodiments, to determine if the selected monoclonal antibodies bind to the target carbonhydrate antigen or epitopes, the antibody can be biotinylated which can then be detected with a streptavidin labeled probe. Anti-carbohydrate antigen antibodies can be tested for reactivity with the carbohydrate by Western blotting.

Hybridomas that produce antibodies that bind, preferably with high affinity, to the carbohydrate antigen, can than be subcloned and further characterized. One clone from each hybridoma, which retains the reactivity of the parent cells (by ELISA), can then be chosen for making a cell bank, and for antibody purification.

Antibodies, or antigen-binding fragments, variants or derivatives thereof of the present disclosure can also be described or specified in terms of their binding affinity to an antigen. The affinity of an antibody for a carbohydrate antigen can be determined experimentally using any suitable method (see, e.g., Berzofsky et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein). The measured affinity of a particular antibody-carbohydrate antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer.

The present antibodies or antigen-binding portions thereof have in vitro and in vivo therapeutic, prophylactic, and/or diagnostic utilities. For example, these antibodies can be administered to cells in culture, e.g., in vitro or ex vivo, or to a subject, e.g., in vivo, to treat, inhibit, prevent relapse, and/or diagnose cancer.

The antibodies or antigen-binding portions thereof can be used on cells in culture, e.g., in vitro or ex vivo. For example, cells can be cultured in vitro in culture medium and contacted by the anti-Globo H antibody or fragment thereof. The methods can be performed on cells present in a subject, as part of an in vivo (e.g., therapeutic or prophylactic) protocol. For in vivo embodiments, the contacting step is effected in a subject and includes administering an anti-toxin antibody or portion thereof to the subject under conditions effective to permit binding of the antibody, or portion thereof, to a carbohydrate antigen (e.g., Globo H) expressed on one or more cancer cells in the subject, e.g., in the breast cancer cell.

The antibody or antigen-binding portion thereof can be administered alone or in combination with another therapeutic agent, e.g., a second monoclonal or polyclonal antibody or antigen-binding portion thereof or a chemotherapeutic agent. The combination product may be a mixture of the two compounds or they may be covalently attached. In one example, the antibody or antigen-binding portion thereof specifically binds to Globo H is combined with an antibody (monoclonal or polyclonal) or antigen-binding portion thereof specifically binds VEGF. In another example, the second agent is a chemotherapy agent (e.g., cyclophosphamide, 5-fluorouracil or Actinomycin-D). The antibodies can also be administered in combinations with a cancer vaccine, e.g., Globo H conjugated with Diphtheria Toxin and a saponin adjuvant.

Methods for Inhibiting Cancer Cells

The invention also provides methods for inhibiting the growth of a cell in vitro, ex vivo or in vivo, wherein the cell, such as a cancer cell, is contacted with an effective amount of an antibody or an antigen-binding portion thereof as described herein. Pathological cells or tissue such as hyperproliferative cells or tissue may be treated by contacting the cells or tissue with an effective amount of an antibody or an antigen-binding portion thereof of this invention. The cells, such as cancer cells, can be primary cancer cells or can be cultured cells available from tissue banks such as the American Type Culture Collection (ATCC). The pathological cells can be cells of a Globo H expressing cancer, gliomas, meningiomas, pituitary adenomas, or a CNS metastasis from a systemic cancer, lung cancer, prostate cancer, breast cancer, hematopoietic cancer or ovarian cancer. The cells can be from a vertebrate, preferably a mammal, more preferably a human. U.S. Patent Publication No. 2004/0087651. Balassiano et al. (2002) Intern. J. Mol. Med. 10:785-788. Thorne, et al. (2004) Neuroscience 127:481-496. Fernandes, et al. (2005) Oncology Reports 13:943-947. Da Fonseca, et al. (2008) Surgical Neurology 70:259267. Da Fonseca, et al. (2008) Arch. Immunol. Ther. Exp. 56:267-276. Hashizume, et al. (2008) Neuroncology 10:112-120. In one embodiment, the cancer is Globo H expressing cancer. In another embodiment, the cancer is SSEA-3 expressing cancer. In yet another embodiment, the cancer is SSEA-4 expressing cancer. Globo H expressing cancer, SSEA-3 expressing cancer and SSEA-4 expressing cancer include, but are not limited to, breast cancer, lung cancer, prostate cancer, pancreatic cancer, gastric cancer, ovarian cancer and endometrial cancer and colon cancer, liver cancer, nasopharyngeal cancer, skin cancer, oral cancer, renal cancer, brain cancer, cervical cancer and bladder cancer.

In vitro efficacy of the present antibody or the antigen-binding portion thereof can be determined using methods well known in the art. For example, the cytoxicity of the antibody or the antigen-binding portion thereof may be studied by MTT [3-(4,5-dimethylthiazol-2-yl)-2,5-diphenyl tetrazolium bromide] cytotoxicity assay. MTT assay is based on the principle of uptake of MTT, a tetrazolium salt, by metabolically active cells where it is metabolized into a blue colored formazon product, which can be read spectrometrically. *J. of Immunological Methods* 65: 55 63, 1983. The cytoxicity of the present antibody or the antigen-binding portion thereof may be studied by colony formation assay. Functional assays for binding Globo H antigen may be performed via ELISA. Cell cycle block by the antibody or the antigen-binding thereof may be studied by standard propidium iodide (PI) staining and flow cytometry. Invasion inhibition may be studied by Boyden chambers. In this assay a layer of reconstituted basement membrane, Matrigel, is coated onto chemotaxis filters and acts as a barrier to the migration of cells in the Boyden chambers. Only cells with invasive capacity can cross the Matrigel barrier. Other assays include, but are not limited to cell viability assays, apoptosis assays, and morphological assays.

Assays can also be done in vivo using a murine model. See, e.g., B. Teicher, Tumor Models for Efficacy Determination. Mol Cancer Ther 2006; 5: 2435-2443."

Pharmaceutical Composition

In one embodiment, the present invention provides pharmaceutical compositions comprising an antibody or antigen-binding portion thereof described herein, and a pharmaceutically acceptable carrier. In another embodiment, the pharmaceutical composition comprises an isolated nucleic acid encoding the present antibody or antigen-binding portion thereof, and a pharmaceutically acceptable carrier. Pharmaceutically acceptable carriers include any and all solvents, dispersion media, isotonic and absorption delaying agents, and the like that are physiologically compatible. In one embodiment, the composition is effective to inhibit cancer cells in a subject.

Routes of administration of the present pharmaceutical compositions include, but are not limited to, intravenous, intramuscular, intransal, subcutaneous, oral, topical, subcutaneous, intradermal, transdermal, subdermal, parenteral, rectal, spinal, or epidermal administration.

The pharmaceutical compositions of the present invention can be prepared as injectables, either as liquid solutions or suspensions, or as solid forms which are suitable for solution or suspension in liquid vehicles prior to injection. The pharmaceutical composition can also be prepared in solid form, emulsified or the active ingredient encapsulated in liposome vehicles or other particulate carriers used for sustained delivery. For example, the pharmaceutical composition can be in the form of an oil emulsion, water-in-oil emulsion, water-in-oil-in-water emulsion, site-specific emulsion, long-residence emulsion, stickyemulsion, microemulsion, nanoemulsion, liposome, microparticle, microsphere, nanosphere, nanoparticle and various natural or synthetic polymers, such as nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures, that allow for sustained release of the pharmaceutical composition.

The present antibodies or antigen-binding portions thereof are formulated into pharmaceutical compositions for delivery to a mammalian subject. The pharmaceutical composition is administered alone, and/or mixed with a pharmaceutically acceptable vehicle, excipient or carrier. Suitable vehicles are, for example, water, saline, dextrose, glycerol, ethanol, or the like, and combinations thereof. In addition, the vehicle can contain minor amounts of auxiliary substances such as wetting or emulsifying agents, pH buffering agents, or adjuvants. Pharmaceutically acceptable carriers can contain a physiologically acceptable compound that acts to, e.g., stabilize, or increase or decrease the absorption or clearance rates of the pharmaceutical compositions of the invention. Physiologically acceptable compounds can include, e.g., carbohydrates, such as glucose, sucrose, or dextrans, antioxidants, such as ascorbic acid or glutathione, chelating agents, low molecular weight proteins, detergents, liposomal carriers, or excipients or other stabilizers and/or buffers. Other physiologically acceptable compounds include wetting agents, emulsifying agents, dispersing agents or preservatives. See e.g., the 21st edition of Remington's Pharmaceutical Science, Mack Publishing Company, Easton, Pa. ("Remington's"). The pharmaceutical compositions of the present invention can also include ancillary substances, such as pharmacological agents, cytokines, or other biological response modifiers.

Furthermore, the pharmaceutical compositions can be formulated into pharmaceutical compositions in either neutral or salt forms. Pharmaceutically acceptable salts include the acid addition salts (formed with the free amino groups of the active polypeptides) and which are formed with inorganic acids such as, for example, hydrochloric or phosphoric acids, or organic acids such as acetic, oxalic, tartaric, mandelic, and the like. Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Actual methods of preparing such dosage forms are known, or will be apparent, to those skilled in the art. See, e.g., Remington's Pharmaceutical Sciences, Mack Publishing Company, Easton, Pa., 21st edition.

Pharmaceutical compositions can be administered in a single dose treatment or in multiple dose treatments on a schedule and over a time period appropriate to the age, weight and condition of the subject, the particular composition used, and the route of administration, whether the pharmaceutical composition is used for prophylactic or curative purposes, etc. For example, in one embodiment, the pharmaceutical composition according to the invention is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of an antibody according to the invention, e.g., the period of time over which the pharmaceutical composition is administered, can vary, depending on any of a variety of factors, e.g., subject response, etc. For example, the pharmaceutical composition can be administered over a period of time ranging from about one or more seconds to one or more hours, one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

For ease of administration and uniformity of dosage, oral or parenteral pharmaceutical compositions in dosage unit form may be used. Dosage unit form as used herein refers to physically discrete units suited as unitary dosages for the subject to be treated; each unit containing a predetermined quantity of active compound calculated to produce the desired therapeutic effect in association with the required pharmaceutical carrier.

The data obtained from the cell culture assays and animal studies can be used in formulating a range of dosage for use in humans. In one embodiment, the dosage of such compounds lies within a range of circulating concentrations that include the $ED_{50}$ with little or no toxicity. The dosage can vary within this range depending upon the dosage form employed and the route of administration utilized. In another embodiment, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Sonderstrup, Springer, Sem. Immunopathol. 25: 35-45, 2003. Nikula et al., Inhal. Toxicol. 4(12): 123-53, 2000.

An exemplary, non-limiting range for a therapeutically or prophylactically effective amount of an antibody or antigen-binding portion of the invention is from about 0.001 to about 60 mg/kg body weight, about 0.01 to about 30 mg/kg body weight, about 0.01 to about 25 mg/kg body weight, about 0.5 to about 25 mg/kg body weight, about 0.1 to about 20 mg/kg body weight, about 10 to about 20 mg/kg body weight, about 0.75 to about 10 mg/kg body weight, about 1 to about 10 mg/kg body weight, about 2 to about 9 mg/kg body weight, about 1 to about 2 mg/kg body weight, about 3 to about 8 mg/kg body weight, about 4 to about 7 mg/kg body weight, about 5 to about 6 mg/kg body weight, about 8 to about 13 mg/kg body weight, about 8.3 to about 12.5 mg/kg body weight, about 4 to about 6 mg/kg body weight, about 4.2 to about 6.3 mg/kg body weight, about 1.6 to about 2.5 mg/kg body weight, about 2 to about 3 mg/kg body weight, or about 10 mg/kg body weight.

The pharmaceutical composition is formulated to contain an effective amount of the present antibody or antigen-binding portion thereof, wherein the amount depends on the animal to be treated and the condition to be treated. In one embodiment, the present antibody or antigen-binding portion thereof is administered at a dose ranging from about 0.01 mg to about 10 g, from about 0.1 mg to about 9 g, from about 1 mg to about 8 g, from about 2 mg to about 7 g, from about 3 mg to about 6 g, from about 10 mg to about 5 g, from about 20 mg to about 1 g, from about 50 mg to about 800 mg, from about 100 mg to about 500 mg, from about 0.01 µg to about 10 g, from about 0.05 µg to about 1.5 mg, from about 10 µg to about 1 mg protein, from about 30 µg to about 500 µg, from about 40 µg to about 300 µg, from about 0.1 µg to about 200 µg, from about 0.1 µg to about 5 µg, from about 5 µg to about 10 µg, from about 10 µg to about 25 µg, from about 25 µg to about 50 µg, from about 50 µg to about 100 µg, from about 100 µg to about 500 µg, from about 500 µg to about 1 mg, from about 1 mg to about 2 mg. The specific dose level for any particular subject depends upon a variety of factors including the activity of the specific peptide, the age, body weight, general health, sex, diet, time of administration, route of administration, and rate of excretion, drug combination and the severity of the particular disease undergoing therapy and can be determined by one of ordinary skill in the art without undue experimentation.

The present antibodies, antigen-binding portions thereof, pharmaceutical compositions and methods can be used in all vertebrates, e.g., mammals and non-mammals, including human, mice, rats, guinea pigs, hamsters, dogs, cats, cows, horses, goats, sheep, pigs, monkeys, apes, gorillas, chimpanzees, rabbits, ducks, geese, chickens, amphibians, reptiles and other animals.

The following examples of specific aspects for carrying out the present invention are offered for illustrative purposes only, and are not intended to limit the scope of the present invention in any way.

EXAMPLES

Example 1: Hybridoma Fusion and Screening

A classical hybridoma fusion was performed. Mice received their first immunization with Globo H-KLH (Keyhole Limpet Hemocyanin) conjugated with a saponin adjuvant and 3 subsequent boosters on days 7, 14, and 24. Bleedings trials were performed at day 10, 17, 21, and 24 and the serum was tested to check for titres of anti-Globo H antibody. Five mice were found to produce high anti-Globo H IgG and anti-Globo H IgM titers and were used for hybridoma production. Mouse myeloma cells were used for fusion with the mouse splenocytes following procedure of a Köhler and Milstein (Köhler G. and Milstein C, 1975). Hybridoma supernatants were screened by affinity ELISA with 0.2 µg Globo H-ceramide/well. The anti-Globo H Vk9 mAb served as positive controls. The OD of hybridoma clone with no dilution of supernatant >background×2 was selected. Top five hybridoma clones were 1E1, 2C2, 2F8, 3D7, 7A11.

Example 2: Kinetic Analysis of Mouse Monoclonal Antibodies

Kinetic binding experiments were performed at 25° C. with Biacore T100 (GE Healthcare) by single-cycle kinetics (SCK) method and multi-cycle kinetics (MCK) method.

Globo H was immobilized by amine coupling, according to the manufacturer's instruction. The Globo H-amine was diluted to 15 mg/ml in immobilization buffer (10 mM sodium acetate pH4.5) and immobilized at 25° C. using a flow rate of 5 µl/min.

The anti-Globo H antibodies (Globo H-Vk9 mab, Globo H-2C2 mAb and Globo H-3D7 mAb) were diluted in running buffer to 200 nM (50 nM). 200 µl of the 200 nM (50 nM) solution was mixed with 200 µl running buffer to obtain a 100 nM (25 nM) solution. The dilution continued for the following dilution series: 200, 100, 50, 25 and 12.5 nM (analyte concentration: 50 nM, 25 nM, 12.5 nM, 6.25 nM, 3.125 nM). The dilution samples were placed in Rack Positions and tested by MCK and SCK methods. Samples for MCK and SCK series were subjected to 420 seconds dissociation time. The surface was regenerated by a 40 seconds injection of a 10 mM Glycine pH2.0/1.5 (v/v=1) solution. The SCK and MCK data were fitted with a 1:1 binding model with Biacore Evaluation software 2.0.

The results were analyzed for the dissociation constant ($K_D$), which is the measure used to describe the binding strength between antibody and antigen, $k_{on}$(1/Ms), the on-rate at which antibody antigen complexes form, $k_{off}$(1/s), the off-rate at which the antibody antigen complexes dissociate, Rmax, the maximum amount of analyte response. Table 2 shows affinity and kinetic data for anti-Globo H antibodies from the following hybridomas: VK9, 2C2 and 3D7. 3D7 antibody and 2C2 antibody have a higher binding affinity than that of VK9 antibody

TABLE 2

Kinetic data for Anti-Globo H Antibodies

| Hybridoma | $K_D$ (M) | $k_{on}$(1/Ms) | $k_{off}$(1/s) | $R_{max}$ | Chi$^2$ |
|---|---|---|---|---|---|
| VK9 | 1.436E−7 | 2.994E+4 | 4.298E−3 | 68.3 | 8.48 |
| 3D7 | 7.854E−9 | 2.760E+5 | 2.168E−3 | 203.5 | 0.6514 |
| 2C2 | 7.631E−9 | 2.810E+5 | 2.144E−3 | 187.4 | 0.542 |

Example 3: Affinity Analysis of Anti-Globo H Antibodies

The following anti-Globo H antibodies were tested for $EC_{50}$ and % of cell binding: Globo H-VK9 mAb, Globo H-1E1 mAb, Globo H-2C2 mAb, Globo H-2F8 mAb, Globo H-3D7 mAb, Globo H-7A11 mAb.

Procedures:

Affinity ELISA for $EC_{50}$: The wells were coated with 0.2 µg Globo H-ceramide per well on ice. After blocking, the tested antibody from 6.2 ng/ml to 51200 ng/ml was added to the wells. After incubation for 1 hour at room temperature, the excess antibody was removed by washing for 3 times. Goat anti-mouse IgG-HRP (1:533) was added. Color development was quantified in a plate reader at 490 nm. $EC_{50}$ was determined by Prism 5.0 Software.

FACS for % of cell binding with Antibody: The cancer cell lines were prepared for a total of 200,000 cells in 50 µl FACS buffer per tube. The indicated antibody was added to reach a final concentration of 1 µg/ml. After gentle vortex, the tubes were placed on ice and incubated for approximately 1 hr. After washing with FACS buffer, the anti-mouse IgG-PE in FACS buffer was added to reach a final concentration of 4 µg/ml. After gentle vortex, the tubes were placed on ice and incubated for approximately 30 mins. After washing with FACS buffer, the test cells were resuspended in 200 µl of FACS buffer. After performing the flow cytometry, the percent of cell binding were analyzed by WinMDI software. In the histogram plot, incubation of secondary antibody only was used to define the background (M1) and binding (M2) region. Based on the setting of secondary antibody only as background (M1), the percentage of binding region (M2) of the indicated antibody was determined.

Antibody binding to Globo H in breast cancer cell line (MCF-7), lung cancer cell line (LLC1) and pancreatic cell line (HPAC) was evaluated using fluorescence activated cell sorting (FACS) analysis.

Results:

Table 3 summarizes the $EC_{50}$ data of Globo H-2C2 mAb, Globo H-2F8 mAb, Globo H-3D7 mAb, Globo H-7A11 mAb, and Globo H-1E1 mAb. The results show that Globo H-2C2 mAb, Globo H-2F8 mAb, Globo H-3D7 mAb, and Globo H-7A11 mAb are more effective in neutralizing Globo H antigen compared to Globo H-VK9 mAb. FACS analysis shows that Globo H-2C2 mAb and Globo H-3D7 mAb have a higher binding affinity for Globo H antigen on breast cancer cell line compare to Globo H VK9 mAb. In addition, Globo H-2C2 mAb and Globo H-3D7 mAb have a higher binding affinity for Globo H antigen on pancreatic cancer cell line (HPAC) compare to Globo H VK9 mAb. Moreover, Globo H-1E1 mAb, Globo H-2C2 mAb, Globo H-3D7 mAb and Globo H-7A11 mAb have a higher binding affinity for Globo H antigen on lung cancer cell line (LLC1) compare to Globo H VK9 mAb.

TABLE 3

$EC_{50}$ and Binding Affinity of Anti-Globo H Antibodies

| Hybirdoma | ELISA $EC_{50}$ (ng/ml) | MCF-7 % Gated | LLC1 % Gated | HPAC % Gated |
|---|---|---|---|---|
| VK9 | 8915.85 | 82.63 | 7.67 | 33.63 |
| 1E1 | 12914.62 | 70.63 | 14.61 | 24.47 |
| 2C2 | 2161.56 | 87.44 | 10.24 | 39.73 |
| 2F8 | 8691.14 | 65.95 | 8.87 | 12.32 |
| 3D7 | 4072.24 | 86.87 | 11.00 | 34.11 |
| 7A11 | 3478.15 | 59.64 | 16.70 | 15.05 |

The $EC_{50}$ value is the concentration of antibody which neutralizes 50% of Globo H.

Example 4: In Vivo Anti-Tumor Evaluation of Anti-Globo H Antibodies

Nude mice weighing 33 g with human pancreatic cancer (HPAC) xenograft were randomized into the following 6 study groups:

| Groups in FIG. 1 | Treatment | N | Dose | Hybridoma |
|---|---|---|---|---|
| PBS (Control) | PBS (Phosphate Buffered Saline) Alone | 4 | 0.4 µg/g twice a week via intraperitoneal injection | — |
| VK9 | Globo H VK9 mAb | 4 | | Vk9 |
| 2C2 | Globo H 2C2 mAb | 4 | | 2C2 |
| 3D7 | Globo H 3D7 mAb | 4 | | 3D7 |

The mice were observed for a period of 29 days for tumor volume and the results were recorded and summarized in FIG. 1.

Results:

At day 29, the tumor volume was reduced in the following order: VK9=3D7<2C2 groups. The tumor volume in 2C2 group was significantly reduced compare to the control group (P<0.05).

Example 5: In Vivo Anti-Tumor Evaluation of Anti-Globo H Antibodies

Figure 2:
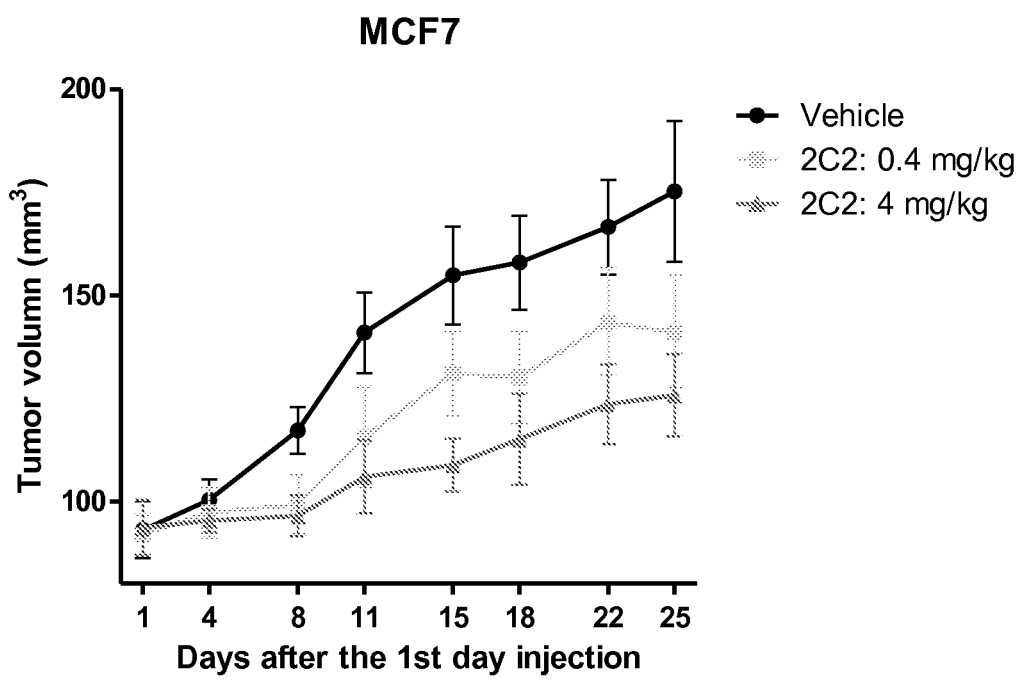
FIG. 2 is a linear plot showing the effect of normal saline and different doses of Globo H-2C2 mAbs on breast cancer (MCF7) volume in mice.

Nude mice weighing 27 g with human breast cancer (MCF7) xenograft were randomized into the following 5 study groups:

| Groups in FIG. 2 | Treatment | N | Dose | Hybridoma |
|---|---|---|---|---|
| Normal Saline (Vehicle) | PBS Alone | 8 | | — |
| 2C2 | Globo H 2C2 mAb | 8 | 0.4 mg/kg on Day 1 | 2C2 |
| 2C2 | Globo H 2C2 mAb | 8 | 4 mg/kg on Day 1 | 2C2 |

The mice were observed for a period of 18 days for tumor volume and the results were recorded and summarized in FIG. 2.

Results:

As shown in FIG. 2, the tumor volume was reduced in the following groups compare to control: 2C2 (4 mg/kg)>2C2 (0.4 mg/kg) after Day 15. Since Day 8, the tumor volume in 2C2 (4 mg/kg) was significantly reduced compare to the control group (P<0.05).

Example 6: Cross Reactivity of Anti-Globo H Antibodies

An in vitro cross reactivity evaluation of Anti-Globo H antibodies (Globo H 2C2, 7A11, 3D7, 2F8, 1E1 mAb and Globo H Vk9) was performed.

Procedure:

GlycoDx cartridges were added with 620 µL wash buffer, 100 µL of diluted Anti-Globo H antibodies, 100 µL blocking buffer, 120 µL conjugate buffer, and 120 µL substrate buffer. The cartridge was detected with the CCD analyzer, and the data is output to the Excel spreadsheet for further analysis.

Results:

As shown in FIG. 3A, Globo H 2C2 mAb binds to Globo H and shows cross reactivity to other carbohydrate antigens, such as the Lewis antigens ($sLe^x$ and $sLe^a$) and S15-S27 antigens (see Table 4 for the list of carbohydrate antigens). Globo H 7A11 mAb binds to Globo H and shows cross reactivity to other carbohydrate antigens, such as the Lewis antigens ($sLe^x$ and $sLe^a$) and S15-S17, S19-S22 antigens (see FIG. 3B). Globo H 3D7 mAb binds to Globo H and shows cross reactivity to other carbohydrate antigens, such as the Lewis antigens ($sLe^x$, $sLe^a$, and $Le^y$) and S15-S22 antigens (see FIG. 3C). Globo H 2F8 mAb binds to Globo H and shows cross reactivity to other carbohydrate antigens, such as the Lewis antigens ($sLe^x$ and $sLe^a$) and S15, S17 and S21 antigens (see FIG. 3D). Globo H 1E1 mAb binds to Globo H and shows cross reactivity to other carbohydrate antigens, such as the Lewis antigens ($sLe^x$) and S16, S17 and S20-S22 antigens (see FIG. 3E) In contrast, Globo H VK9 mAb only binds to Globo H and does not show cross-reactivity to other carbohydrate antigens (see FIG. 3F).

TABLE 4

Figure 3C:
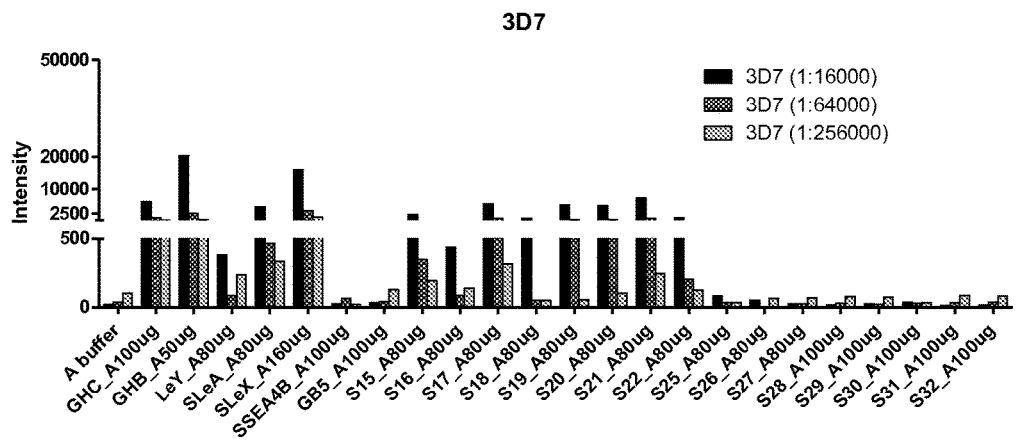
Figure 3D:
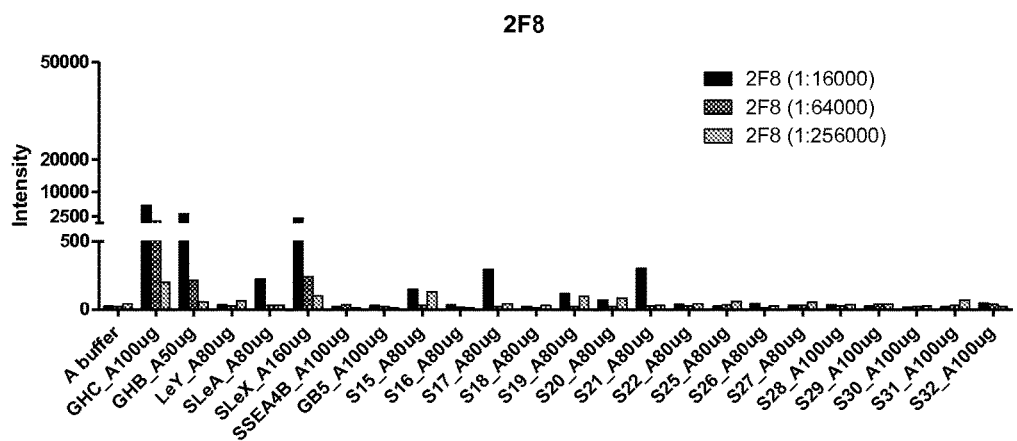
Figure 3E:
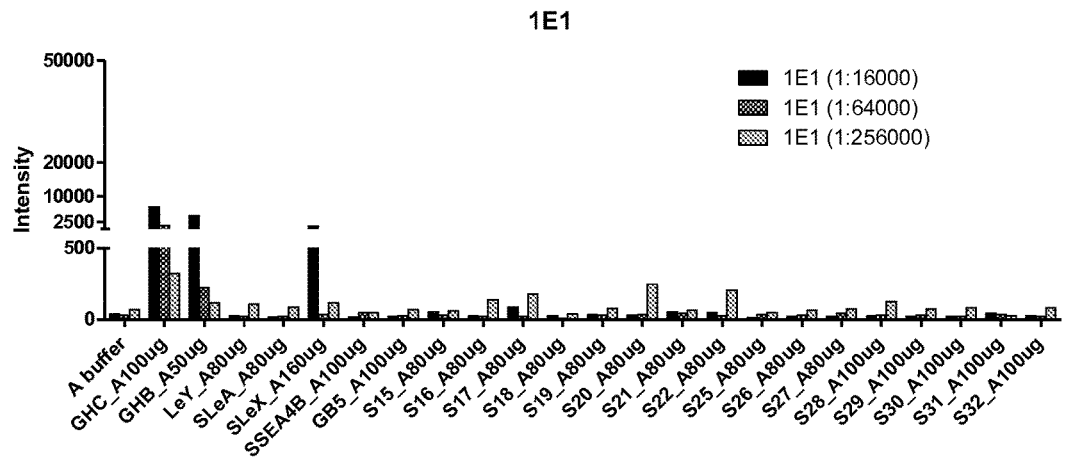
Figure 3F:
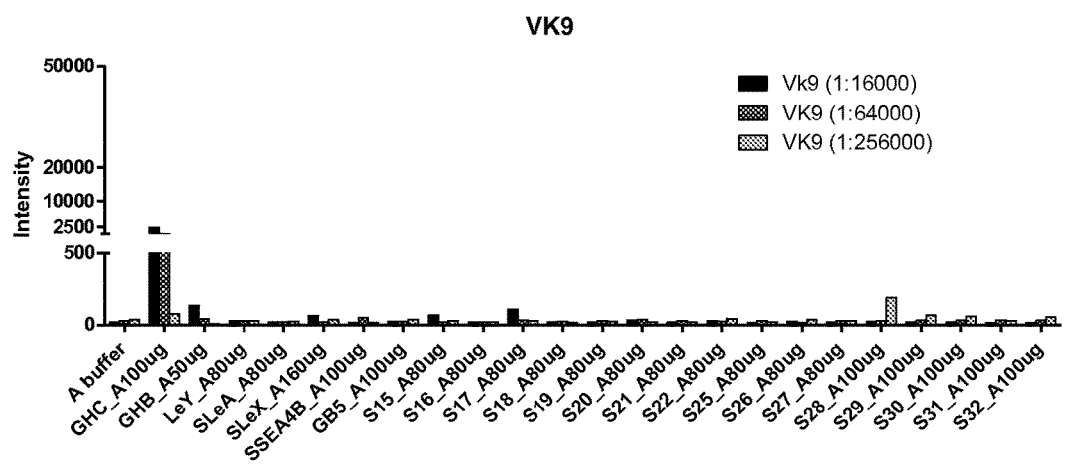

List of carbohydrate antigens in FIG. 3A-3C

| Abbreviation | Carbohyrate Antigen |
|---|---|
| S15 | α-GalNAc(Tn) |
| S16 | α-NeuAc-OCH$_2$C$_6$H$_4$-p- |

TABLE 4-continued

List of carbohydrate antigens in FIG. 3A-3C

| Abbreviation | Carbohyrate Antigen |
|---|---|
| S17 | Fucα1-2Galβ1-4GalNAcβ NHCOOCH₂ (H types3) |
| S18 | NeuAcα2-8NeuAcα, (NeuAcα2-8)2 Polysialic acid |
| S19 | NeuAca2-6Galb |
| S20 | NeuAcb2-6Gala(STn) |
| S21 | Gala1-3Galb1-4GlaNAcb |
| S22 | (NeuAca2-8)3 |
| S25 | 6Gal-HSO3-SiaLex |
| S26 | 6GluNAc-HSO3-SiaLex |
| S27 | α2-6 sialylated diantennary N-glycans |
| S28 | GalNAcβ1-4(NeuAcα2-8NeuAcα2-3)Galβ1-4Glc-β-Nac-spacer 3-Biotin (GD2) |
| S29 | GalNAcβ1-4(NeuAcα2-3)Galβ1-4Glc-β-Nac-spacer 3-Biotin (GM2) |
| S30 (SSEA4) | Neu5Acα2-3Galβ1-3GalNAcβ1-3Galα1-4Galβ1-4Glcβ-Nac-spacer 3-Biotin (SSEA4) |
| S31 | NeuAcα2-8NeuAcα2-3Galβ1-4Glc-β-Nac-spacer 3-Biotin (GD3) |
| S32 | Fucα1-2Galβ1-3GalNAcβ1-4(Neu5Acα2-3)Galβ1-4Glcβ-Nac-spacer 3-Biotin (Fucosyl-GM1) |

Example 7: Binding Affinity of Anti-Globo H Antibody

An in vitro evaluation of the following Anti-Globo H humanized antibodies was performed. Table 5 lists the amino acid sequences of the heavy chain regions and light chain regions of the humanized antibody from hybridoma 2C2.

TABLE 5

Amino acid sequences of 2C2 humanized antibody

| Light Chain Region or Heavy Chain Region | Amino Acid Sequence |
|---|---|
| Light Chain 2 | FW1: LSPGERATLSC (SEQ ID NO: 88)<br>CDR1: RASSSVSYMH (SEQ ID NO: 8)<br>FW2: WYQQKPGSSPKPWIY (SEQ ID NO: 12)<br>CDR2: ATSNLAS (SEQ ID NO: 9)<br>FW3: GVPSRFSGSGSGTDFTFTISSLQPEDIATYYC (SEQ ID NO: 90)<br>CDR3: QQWSRNPFT (SEQ ID NO: 10) |
| Light Chain 2-22 | FW1: SEQ ID NO: 88<br>CDR1: SEQ ID NO: 8<br>FW2: WYQQKPGSSPKLWIY<br>CDR2: SEQ ID NO: 9<br>FW3: SEQ ID NO: 90<br>CDR3: SEQ ID NO: 10 |
| Light Chain 2-23 | FW1: SEQ ID NO: 88<br>CDR1: SEQ ID NO: 8<br>FW2: WYQQKPGSSPKPLIY<br>CDR2: SEQ ID NO: 9<br>FW3: SEQ ID NO: 90<br>CDR3: SEQ ID NO: 10 |
| Heavy Chain 2 | FW1: SGPTLVKPTQTLTLTCTFSGFSL (SEQ ID NO: 87)<br>CDR1: YTFDMGVG (SEQ ID NO: 5)<br>FW 2: WIRQPSGKGLEWLA (SEQ ID NO: 11)<br>CDR 2: HIWWDDDKYYNPALKS (SEQ ID NO: 6)<br>FW3: RLTISKDTSKNQVVLTMTNMDPVDTATYYCAR (SEQ ID NO: 89)<br>CDR 3: VRGLHDYYYWFAY (SEQ ID NO: 7) |
| Heavy Chain 2-21 | FW1: SEQ ID NO: 87<br>CDR1: SEQ ID NO: 5<br>FW 2: WIRQPPGKGLEWLA<br>CDR 2: SEQ ID NO: 6<br>FW3: SEQ ID NO: 89<br>CDR 3: SEQ ID NO: 7 |
| Heavy Chain 2-22 | FW1: SEQ ID NO: 87<br>CDR1: SEQ ID NO: 5<br>FW 2: WIRQPSGKALEWLA<br>CDR 2: SEQ ID NO: 6<br>FW3: SEQ ID NO: 89<br>CDR 3: SEQ ID NO: 7 |

The results of the binding affinity by ELISA method are listed in Tables 6-9.

TABLE 6

The binding affinity of an antibody with a chimeric light chain and a humanized heavy chain.

| Light Chain | Heavy Chain | Affinity ELISA (optical density) |
|---|---|---|
| Chimeric light chain (SEQ ID NO: 4) | Heavy Chain 2-22 | 0.17 |
| Chimeric light chain (SEQ ID NO: 4) | Heavy Chain 2 | 0.4 |

These results show that the alteration of the amino acid at position 9 (from G to A) in FW2 of the heavy chain reduces the binding affinity of the antibody from 0.4 to 0.17.

TABLE 7

The bindinig affinity of an antibody with a humanized light chain and a humanized heavy chain

| Light Chain | Heavy Chain | Affinity ELISA (optical density) |
|---|---|---|
| Light chain 2 | Heavy Chain 2 | 0.42 |
| Light Chain 2-22 | Heavy Chain 2 | 0.08 |
| Light Chain 2-23 | Heavy Chain 2 | 0.09 |

TABLE 8

The bindinig affinity of an antibody with a humanized light chain and a humanized heavy chain

| Light Chain | Heavy Chain | Affinity ELISA (optical density) |
|---|---|---|
| Light chain 2 | Heavy Chain 2-21 | 0.53 |
| Light Chain 2-22 | Heavy Chain 2-21 | 0.08 |
| Light Chain 2-23 | Heavy Chain 2-21 | 0.12 |

TABLE 9

The bindinig affinity of an antibody with a humanized light chain and a humanized heavy chain

| Light Chain | Heavy Chain | Affinity ELISA (optical density) |
|---|---|---|
| Light chain 2 | Heavy Chain 2-22 | 0.32 |
| Light Chain 2-22 | Heavy Chain 2-22 | 0.07 |
| Light Chain 2-23 | Heavy Chain 2-22 | 0.08 |

These results show the alteration of the amino acid at position 12 of FW2 of the light chain (from P to L) reduces the binding affinity from 0.32-0.53 to 0.07-0.08, and the alteration of amino acid at position 13 of FW2 of the light chain (from W to L) reduces the binding affinity from 0.32-0.53 to 0.08-0.12.

While specific aspects of the invention have been described and illustrated, such aspects should be considered illustrative of the invention only and not as limiting the invention as construed in accordance with the accompanying claims. All publications and patent applications cited in this specification are herein incorporated by reference in their entirety for all purposes as if each individual publication or patent application were specifically and individually indicated to be incorporated by reference in its entirety for all purposes. Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

| | | Sequense Listing: SEQ ID NO. 1-90 | |
|---|---|---|---|
| Hybridoma Clones | Chain Region | Sequence | SEQ ID No. |
| 2C2 | Heavy Chain Variable Region (Vh) | Nucleic acid Sequence<br>TCTGGCCCTGGGATATTGCAGCCCTCCCA<br>GACCCTCAGTCTGACTTGTTCTTTCTCTG<br>GATTTTCACTGTACACTTTTGATATGGGT<br>GTAGGCTGGATTCGTCAGCCTTCAGGGA<br>AGGGTCTGGAGTGGCTGGCACACATTTG<br>GTGGGATGATGATAAGTACTATAACCCA<br>GCCCTGAAGAGTCGGCTCACAGTCTCCA<br>AGGATACCTCCAAAAACCAGGTCTTCCT<br>CAAGATCCCCAATGTGGACACTGCAGAT<br>AGTGCCACATACTACTGTGCTCGAGTAA<br>GGGGCCTCCATGATTATTACTACTGGTTT<br>GCTTACTGGGGCCAAGGGACTCTGGTCA<br>CTGTCTCT | 1 |
| 2C2 | Light Chain Variable Region (VL) | Nucleic acid Sequence<br>GCATCTCCAGGGGAGAAGGTCACAATGA<br>CTTGCAGGGCCAGTTCAAGTGTAAGTTA<br>CATGCACTGGTACCAGCAGAAGCCAGGA<br>TCCTCCCCCAAACCCTGGATTTATGCCAC<br>ATCCAACCTGGCGTCTGGAGTCCCTGCTC<br>GCTTCAGTGGCAGTGGGTCTGGGACCTCT<br>TACTCTCTCACAATCAGCAGAGTGGAGG<br>CTGAAGATGCTGCCACTTATTTCTGCCAG<br>CAGTGGAGTCGAAACCCATTCACGTTCG<br>GCTCGGGGACAAAGTTGGAAATAAGA | 2 |
| 2C2 | Heavy Chain Variable Region (Vh) | Amino Acid Sequence<br>SGPG ILQPSQTLSL TCSFSGFSLY<br>TFDMGVGWIR QPSGKGLEWL<br>AHIWWDDDKY YNPALKSRLT<br>VSKDTSKNQV FLKIPNVDTA<br>DSATYYCARV RGLHDYYYWF<br>AYWGQGTLVT VS | 3 |
| 2C2 | Light Chain (VL) | Amino Acid Sequence<br>ASPGEKVT MTCRASSSVS<br>YMHWYQQKPG SSPKPWIYAT<br>SNLASGVPAR FSGSGSGTSY SLTISRVEAE<br>DAATYFCQQW SRNPFTFGSG TKLEIR | 4 |
| 2C2 | Heavy Chain CDR1 | Amino Acid Sequence<br>YTFDMGVG | 5 |

-continued

| Sequense Listing: SEQ ID NO. 1-90 | | | |
|---|---|---|---|
| Hybridoma Clones | Chain Region | Sequence | SEQ ID No. |
| 2C2 | Heavy Chain CDR2 | Amino Acid Sequence HIWWDDDKYYNPALKS | 6 |
| 2C2 | Heavy Chain CDR3 | Amino Acid Sequence VRGLHDYYYWFAY | 7 |
| 2C2 | Light Chain CDR1 | Amino Acid Sequence RASSSVSYMH | 8 |
| 2C2 | Light Chain CDR2 | Amino Acid Sequence ATSNLAS | 9 |
| 2C2 | Light Chain CDR3 | Amino Acid Sequence QQWSRNPFT | 10 |
| 2C2 | Heavy Chain Frame work 2 | Amino Acid Sequence WIRQPSGKGLEWLA | 11 |
| 2C2 | Light Chain Frame work 2 | Amino Acid Sequence WYQQKPGSSPKPWIY | 12 |
| 3D7 | Heavy Chain Variable Region (Vh) | Amino Acid Sequence SGPGILQPSQTLSLTCSFSGFSLYTFDMGVG WIRQPSGKGLEWLAHIWWDDDKYYNPAL KSRLTVSKDTSKNQVFLKIPNVDTADSAT YYCARVRGLHDYYYWFAYWGQGTLVTV S | 13 |
| 3D7 | Light Chain Variable Region (VL) | Amino Acid Sequence ASPGEKVTMTCRASSSVSYMHWYQQKPG SSPKPWIYATSNLASGVPARFSGSGSGTSY SLTISRVEAEDAATYFCQQWSRNPFTFGSG TKLEIR | 14 |
| 3D7 | Heavy Chain CDR1 | Amino Acid Sequence YTFDMGVG | 15 |
| 3D7 | Heavy Chain CDR2 | Amino Acid Sequence HIWWDDDKYYNPALKS | 16 |
| 3D7 | Heavy Chain CDR3 | Amino Acid Sequence VRGLHDYYYWFAY | 17 |
| 3D7 | Light Chain CDR1 | Amino Acid Sequence RASSSVSYMH | 18 |
| 3D7 | Light Chain CDR2 | Amino Acid Sequence ATSNLAS | 19 |
| 3D7 | Light Chain CDR3 | Amino Acid Sequence QQWSRNPFT | 20 |
| 7A11 | Heavy Chain Variable Region (Vh) | Amino Acid Sequence SGPGILQPSQTLSLYTFDMGVG WIRQPSGKGLEWLAIWWDDDKYYNPGL KSRLTISKDTSKNQVFLKIPNVDTADSATY YCARIRGLRDYYYWFAYWGQGTLVTVS | 21 |

-continued

| Sequense Listing: SEQ ID NO. 1-90 | | | |
|---|---|---|---|
| Hybridoma Clones | Chain Region | Sequence | SEQ ID No. |
| 7A11 | Light Chain Variable Region (VL) | Amino Acid Sequence ASPGEKVTMTCRASSSVSYMHWYQQKPG SSPKPWIYATSNLASGVPARFSGSGSGTSY SLTISRVEAEDAATYFCQQWSRNPFTFGSG TKLEIR | 22 |
| 7A11 | Heavy Chain CDR1 | Amino Acid Sequence YTFDMGVG | 23 |
| 7A11 | Heavy Chain CDR2 | Amino Acid Sequence QIWWDDDKYYNPGLKS | 24 |
| 7A11 | Heavy Chain CDR3 | Amino Acid Sequence IRGLRDYYYWFAY | 25 |
| 7A11 | Light Chain CDR1 | Amino Acid Sequence RASSSVSYMH | 26 |
| 7A11 | Light Chain CDR2 | Amino Acid Sequence ATSNLAS | 27 |
| 7A11 | Light Chain CDR3 | Amino Acid Sequence QQWSRNPFT | 28 |
| 2F8 | Heavy Chain Variable Region (Vh) | Amino Acid Sequence SGPGILQPSQTLSLTCSFSGFSLSTFGLGVG WIRQPSGKGLEWLAHIWWDDDKSYNPAL KSRLTISKDTSKNQVFLMIANVDTADTATY YCARIGPKWSNYYYYCDYWGQGTTLTVS | 29 |
| 2F8 | Light Chain Variable Region (VL) | Amino Acid Sequence ASPGEKVTMTCRASSSVSYMHWYQQKPG SSPKPYIYATSNLSSGVPARFSGSGSGTSYS LTISRVEAEDAATYYCQQWSSNPFTFGSGT KLEIK | 30 |
| 2F8 | Heavy Chain CDR1 | Amino Acid Sequence STFGLGVG | 31 |
| 2F8 | Heavy Chain CDR2 | Amino Acid Sequence HIWWDDDKSYNPALKS | 32 |
| 2F8 | Heavy Chain CDR3 | Amino Acid Sequence IGPKWSNYYYYCDY | 33 |
| 2F8 | Light Chain CDR1 | Amino Acid Sequence RASSSVSYMH | 34 |
| 2F8 | Light Chain CDR2 | Amino Acid Sequence ATSNLSS | 35 |
| 2F8 | Light Chain CDR3 | Amino Acid Sequence QQWSSNPFT | 36 |
| 1E1 | Heavy Chain Variable Region (Vh) | Amino Acid Sequence SGPGILQPSQTLSLTCSFSGFSLSTFGLGVG WIRQPSGKGLEWLAHIWWDDDKSYNPAL KSQLTISKDTSKNQVLLKIANVDTADTATY YCARIGPKWSNYYYYCDYWGQGTTLTVS | 37 |

-continued

| Sequense Listing: SEQ ID NO. 1-90 | | | |
|---|---|---|---|
| Hybridoma Clones | Chain Region | Sequence | SEQ ID No. |
| 1E1 | Light Chain Variable Region (VL) | Amino Acid Sequence<br>ASPGEKVTMTCRASSSVSYMHWYQQKPG<br>SSPKPYIYATSNLSSGVPARFSGSGSGTSYS<br>LTISRVEAEDAATYYCQQWSSNPFTFGSGT<br>KLEIK | 38 |
| 1E1 | Heavy Chain CDR1 | Amino Acid Sequence<br>STFGLGVG | 39 |
| 1E1 | Heavy Chain CDR2 | Amino Acid Sequence<br>HIWWDDDKSYNPALKS | 40 |
| 1E1 | Heavy Chain CDR3 | Amino Acid Sequence<br>IGPKWSNYYYYCDY | 41 |
| 1E1 | Light Chain CDR1 | Amino Acid Sequence<br>RASSSVSYMH | 42 |
| 1E1 | Light Chain CDR2 | Amino Acid Sequence<br>ATSNLSS | 43 |
| 1E1 | Light Chain CDR3 | Amino Acid Sequence<br>QQWSSNPFT | 44 |
| 2C2 | Heavy Chain CDR1 | Nucleic Acid Sequence<br>TACACTTTTGATATGGGTGTAGGC | 45 |
| 2C2 | Heavy Chain CDR2 | Nucleic Acid Sequence<br>CACATTTGGTGGGATGATGATAAGTACT<br>ATAACCCAGCCCTGAAGAGT | 46 |
| 2C2 | Heavy Chain CDR3 | Nucleic Acid Sequence<br>GTAAGGGGCCTCCATGATTATTACTACTG<br>GTTTTGCTTAC | 47 |
| 2C2 | Light Chain CDR1 | Nucleic Acid Sequence<br>AGGGCCAGTTCAAGTGTAAGTTACATGC<br>AC | 48 |
| 2C2 | Light Chain CDR2 | Nucleic Acid Sequence<br>GCCACATCCAACCTGGCGTCT | 49 |
| 2C2 | Light Chain CDR3 | Nucleic Acid Sequence<br>CAGCAGTGGAGTCGAAACCCATTCACG | 50 |
| 3D7 | Heavy Chain Variable Region (Vh) | Nucleic Acid Sequence<br>TCTGGCCCTGGGATATTGCAGCCCTCCCA<br>GACCCTCAGTCTGACTTGTTCTTTCTCTG<br>GATTTTCACTGTACACTTTTGATATGGGT<br>GTAGGCTGGATTCGTCAGCCTTCAGGGA<br>AGGGTCTGGAGTGGCTGGCACACATTTG<br>GTGGGATGATGATAAGTACTATAACCCA<br>GCCCTGAAGAGTCGGCTCACAGTCTCCA<br>AGGATACCTCCAAAAACCAGGTCTTCCT<br>CAAGATCCCCAATGTGGACACTGCAGAT<br>AGTGCCACATACTACTGTGCTCGAGTAA<br>GGGGCCTCCATGATTATTACTACTGGTTT<br>GCTTACTGGGGCCAAGGGACTCTGGTCA<br>CTGTCTCT | 51 |
| 3D7 | Light Chain Variable Region | Nucleic Acid Sequence<br>GCATCTCCAGGGGAGAAGGTCACAATGA<br>CTTGCAGGGCCAGTTCAAGTGTAAGTTA<br>CATGCACTGGTACCAGCAGAAGCCAGGA | 52 |

| Sequense Listing: SEQ ID NO. 1-90 | | | |
|---|---|---|---|
| Hybridoma Clones | Chain Region | Sequence | SEQ ID No. |
| | (VL) | TCCTCCCCCAAACCCTGGATTTATGCCAC ATCCAACCTGGCGTCTGGAGTCCCTGCTC GCTTCAGTGGCAGTGGGTCTGGGACCTCT TACTCTCTCACAATCAGCAGAGTGGAGG CTGAAGATGCTGCCACTTATTTCTGCCAG CAGTGGAGTCGAAACCCATTCACGTTCG GCTCGGGGACAAAGTTGGAAATAAGA | |
| 3D7 | Heavy Chain CDR1 | Nucleic Acid Sequence TACACTTTTGATATGGGTGTAGGC | 53 |
| 3D7 | Heavy Chain CDR2 | Nucleic Acid Sequence CACATTTGGTGGGATGATGATAAGTACT ATAACCCAGCCCTGAAGAGT | 54 |
| 3D7 | Heavy Chain CDR3 | Nucleic Acid Sequence GTAAGGGGCCTCCATGATTATTACTACTG GTTTGCTTAC | 55 |
| 3D7 | Light Chain CDR1 | Nucleic Acid Sequence AGGGCCAGTTCAAGTGTAAGTTACATGC AC | 56 |
| 3D7 | Light Chain CDR2 | Nucleic Acid Sequence GCCACATCCAACCTGGCGTCT | 57 |
| 3D7 | Light Chain CDR3 | Nucleic Acid Sequence CAGCAGTGGAGTCGAAACCCATTCACG | 58 |
| 7A11 | Heavy Chain Variable Region (Vh) | Nucleic Acid Sequence TCTGGCCCTGGGATATTGCAGCCCTCCCA GACCCTCAGTCTGACTTGTTCTTTCTCTG GATTTTCACTGTACACTTTTGATATGGGT GTAGGCTGGATTCGTCAGCCTTCAGGGA AGGGTCTGGAGTGGCTGGCACAAATTTG GTGGGATGATGATAAGTACTATAACCCA GGCCTGAAGAGTCGGCTCACAATCTCCA AGGATACCTCCAAAAACCAGGTATTCCT CAAGATCCCAATGTGGACACTGCAGAT AGTGCCACATACTACTGTGCTCGAATAA GGGGCCTCCGTGATTATTACTACTGGTTT GCTTACTGGGGCCAAGGGACTCTGGTCA CTGTCTCT | 59 |
| 7A11 | Light Chain Variable Region (VL) | Nucleic Acid Sequence GCATCTCCAGGGGAGAAGGTCACAATGA CTTGCAGGGCCAGCTCAAGTGTAAGTTA CATGCACTGGTACCAGCAGAAGCCAGGA TCCTCCCCCAAACCCTGGATTTATGCCAC ATCCAACCTGGCTTCTGGAGTCCCTGCTC GCTTCAGTGGCAGTGGGTCTGGGACCTCT TACTCTCTCACAATCAGCAGAGTGGAGG CTGAAGATGCTGCCACTTATTTCTGCCAG CAGTGGAGTCGAAACCCATTCACGTTCG GCTCGGGGACAAAGTTGGAAATAAGA | 60 |
| 7A11 | Heavy Chain CDR1 | Nucleic Acid Sequence TACACTTTTGATATGGGTGTAGGC | 61 |
| 7A11 | Heavy Chain CDR2 | Nucleic Acid Sequence CAAATTTGGTGGGATGATGATAAGTACT ATAACCCAGGCCTGAAGAGT | 62 |
| 7A11 | Heavy Chain CDR3 | Nucleic Acid Sequence ATAAGGGGCCTCCGTGATTATTACTACTG GTTTGCTTAC | 63 |
| 7A11 | Light Chain CDR1 | Nucleic Acid Sequence AGGGCCAGCTCAAGTGTAAGTTACATGC AC | 64 |

| Hybridoma Clones | Chain Region | Sequence | SEQ ID No. |
|---|---|---|---|
| 7A11 | Light Chain CDR2 | Nucleic Acid Sequence<br>GCCACATCCAACCTGGCTTCT | 65 |
| 7A11 | Light Chain CDR3 | Nucleic Acid Sequence<br>CAGCAGTGGAGTCGAAACCCATTCACG | 66 |
| 2F8 | Heavy Chain Variable Region (Vh) | Nucleic Acid Sequence<br>TCTGGCCCTGGGATATTGCAGCCCTCCCA<br>GACCCTCAGTCTGACTTGTTCTTTCTCTG<br>GGTTTTCGCTGAGCACTTTTGGTTTGGGT<br>GTAGGCTGGATTCGTCAGCCTTCAGGGA<br>AGGGTCTGGAGTGGCTGGCACACATTTG<br>GTGGGATGATGATAAGTCCTATAACCCA<br>GCCCTGAAGAGTCGGCTCACAATCTCCA<br>AGGATACCTCCAAAAACCAGGTCTTCCT<br>CATGATCGCCAATGTGGACACTGCAGAT<br>ACTGCCACATACTACTGTGCTCGAATAG<br>GCCCGAAATGGAGCAACTACTACTACTA<br>CTGTGACTACTGGGGCCAAGGCACCACT<br>CTCACAGTCTCC | 67 |
| 2F8 | Light Chain Variable Region (VL) | Nucleic Acid Sequence<br>GCATCTCCAGGGGAGAAGGTCACAATGA<br>CTTGCAGGGCCAGCTCAAGTGTTAGTTAC<br>ATGCACTGGTACCAGCAGAAGCCAGGAT<br>CCTCCCCCAAACCCTACATTTATGCCACA<br>TCCAACCTGTCTTCTGGAGTCCCTGCTCG<br>CTTCAGTGGCAGTGGGTCTGGGACCTCTT<br>ACTCTCTCACAATCAGCAGAGTGGAGGC<br>TGAAGATGCTGCCACTTATTACTGCCAGC<br>AGTGGAGTAGTAACCCCTTCACGTTCGG<br>CTCGGGGACAAAGTTGGAAATAAAA | 68 |
| 2F8 | Heavy Chain CDR1 | Nucleic Acid Sequence<br>AGCACTTTTGGTTTGGGTGTAGGC | 69 |
| 2F8 | Heavy Chain CDR2 | Nucleic Acid Sequence<br>CACATTTGGTGGGATGATGATAAGTCCT<br>ATAACCCAGCCCTGAAGAGT | 70 |
| 2F8 | Heavy Chain CDR3 | Nucleic Acid Sequence<br>ATAGGCCCGAAATGGAGCAACTACTACT<br>ACTACTGTGACTAC | 71 |
| 2F8 | Light Chain CDR1 | Nucleic Acid Sequence<br>AGGGCCAGCTCAAGTGTTAGTTACATGC<br>AC | 72 |
| 2F8 | Light Chain CDR2 | Nucleic Acid Sequence<br>GCCACATCCAACCTGTCTTCT | 73 |
| 2F8 | Light Chain CDR3 | Nucleic Acid Sequence<br>CAGCAGTGGAGTAGTAACCCCTTCACG | 74 |
| 1E1 | Heavy Chain Variable Region (Vh) | Nucleic Acid Sequence<br>TCTGGCCCTGGGATATTGCAGCCCTCCCA<br>GACCCTCAGTCTGACTTGTTCTTTCTCTG<br>GGTTTTCGCTGAGCACTTTTGGTTTGGGT<br>GTAGGCTGGATTCGTCAGCCTTCAGGGA<br>AGGGTCTGGAGTGGCTGGCACACATTTG<br>GTGGGATGATGATAAGTCCTATAACCCA<br>GCCCTGAAGAGTCAGCTCACAATCTCCA<br>AGGATACCTCCAAAAACCAGGTACTCCT<br>CAAGATCGCCAATGTGGACACTGCAGAT<br>ACTGCCACATACTACTGTGCTCGAATAG<br>GCCCGAAATGGAGCAACTACTACTACTA<br>CTGTGACTACTGGGGCCAAGGCACCACT<br>CTCACAGTCTCC | 75 |

-continued

| Sequense Listing: SEQ ID NO. 1-90 | | | |
|---|---|---|---|
| Hybridoma Clones | Chain Region | Sequence | SEQ ID No. |
| 1E1 | Light Chain Variable Region (VL) | Nucleic Acid Sequence<br>GCATCTCCAGGGGAGAAGGTCACAAT<br>GACTTGCAGGGCCAGCTCAAGTGTTAG<br>TTACATGCACTGGTACCAGCAGAAGCC<br>AGGATCCTCCCCCAAACCCTACATTTA<br>TGCCACATCCAACCTGTCTTCTGGAGT<br>CCCTGCTCGCTTCAGTGGCAGTGGGTC<br>TGGGACCTCTTACTCTCTCACAATCAG<br>CAGAGTGGAGGCTGAAGATGCTGCCA<br>CTTATTACTGCCAGCAGTGGAGTAGTA<br>ACCCCTTCACGTTCGGCTCGGGGACAA<br>AGTTGGAAATAAAA | 76 |
| 1E1 | Heavy Chain CDR1 | Nucleic Acid Sequence<br>AGCACTTTTGGTTTGGGTGTAGGC | 77 |
| 1E1 | Heavy Chain CDR2 | Nucleic Acid Sequence<br>CACATTTGGTGGGATGATGATAAGTCCT<br>ATAACCCAGCCCTGAAGAGT | 78 |
| 1E1 | Heavy Chain CDR3 | Nucleic Acid Sequence<br>ATAGGCCCGAAATGGAGCAACTACTACT<br>ACTACTGTGACTAC | 79 |
| 1E1 | Light Chain CDR1 | Nucleic Acid Sequence<br>AGGGCCAGCTCAAGTGTTAGTTACATGC<br>AC | 80 |
| 1E1 | Light Chain CDR2 | Nucleic Acid Sequence<br>GCCACATCCAACCTGTCTTCT | 81 |
| 1E1 | Light Chain CDR3 | Nucleic Acid Sequence<br>CAGCAGTGGAGTAGTAACCCCTTCACG | 82 |
| 2C2 | Heavy Chain Frame work 1 | Amino Acid Sequence<br>SGPGILQPSQTLSLTCSFSGFSL | 83 |
| 2C2 | Light Chain Frame work 1 | Amino Acid Sequence<br>ASPGEKVTMTC | 84 |
| 2C2 | Heavy Chain Frame work 3 | Amino Acid Sequence<br>RLTVSKDTSKNQVFLKIPNVDTA<br>DSATYYCAR | 85 |
| 2C2 | Light Chain Frame work 3 | Amino Acid Sequence<br>GVPARFSGSGSGTSYSLTISRVEAE<br>DAATYFC | 86 |
| 2C2 | Heavy Chain Frame work 1 | Amino Acid Sequence of Humanized Antibody<br>SGPTLVKPTQTLTLTCTFSGFSL | 87 |
| 2C2 | Light Chain Frame work 1 | Amino Acid Sequence of Humanized Antibody<br>LSPGERATLSC | 88 |
| 2C2 | Heavy Chain Frame work 3 | Amino Acid Sequence of Humanized Antibody<br>RLTISKDTSKNQVVLTMTNMDPVDTATYY<br>CAR | 89 |

| Hybridoma Clones | Chain Region | Sequence | SEQ ID No. |
|---|---|---|---|
| 2C2 | Light Chain Frame work 3 | Amino Acid Sequence of Humanized Antibody GVPSRFSGSGSGTDFTFTISSLQPEDIATYY C | 90 |

What is claimed is:

1. An antibody, or an antigen-binding portion thereof, comprising:
    a first heavy chain complementarity determining region (HCDR1) having the amino acid sequence of SEQ ID NO:5,
    a second heavy chain complementarity determining region (HCDR2) having the amino acid sequence of SEQ ID NO: 6,
    a third heavy chain complementarity determining region (HCDR3) having the amino acid sequence of SEQ ID NO:7,
    a first light chain complementarity determining region (LCDR1) having the amino acid sequence of SEQ ID NO:8,
    a second light chain complementarity determining region (LCDR2) having the amino acid sequence of SEQ ID NO:9 and
    a third light chain complementarity determining region (LCDR3) having the amino acid sequence of SEQ ID NO: 10,
    wherein said antibody, or antigen-binding portion thereof, binds to Globo H.

2. The antibody or the antigen-binding portion thereof of claim 1, further comprising a framework about 80% to about 100% homologous to the amino acid sequence of SEQ ID NO:11, wherein the framework is between HCDR1 and HCDR2.

3. The antibody or the antigen-binding portion thereof of claim 1, further comprising a framework about 80% to about 100% homologous to the amino acid sequence of SEQ ID NO:12, wherein the framework is between LCDR1 and LCDR2.

4. An antibody, or an antigen-binding portion thereof, comprising:
    a HCDR1 having the amino acid sequence of SEQ ID NO:5,
    a HCDR2 having the amino acid sequence of SEQ ID NO:24,
    a HCDR3 having the amino acid sequence of SEQ ID NO:25,
    a LCDR1 having the amino acid sequence of SEQ ID NO: 8,
    a LCDR2 having the amino acid sequence of SEQ ID NO:9, and
    a LCDR3 having the amino acid sequence of SEQ ID NO: 10,
    wherein said antibody, or antigen-binding portion thereof, binds to Globo H.

5. An antibody, or an antigen-binding portion thereof, comprising:
    a HCDR1 having the amino acid sequence of SEQ ID NO:31,
    a HCDR2 having the amino acid sequence of SEQ ID NO:32,
    a HCDR3 having the amino acid sequence of SEQ ID NO:33,
    a LCDR1 having the amino acid sequence of SEQ ID NO:8,
    a LCDR2 having the amino acid sequence of SEQ ID NO:35,
    and a LCDR3 having the amino acid sequence of SEQ ID NO:36,
    wherein said antibody, or antigen-binding portion thereof, binds to Globo H.

6. An antibody, or an antigen-binding portion thereof, comprising:
    a heavy chain variable domain comprising the amino acid sequence of SEQ ID NO:3; and
    a light chain variable domain comprising the amino acid sequence of SEQ ID NO: 4,
    wherein said antibody, or antigen-binding portion thereof, binds to Globo H.

7. An antibody, or an antigen-binding portion thereof, comprising:
    a heavy chain variable domain comprising the amino acid sequence of SEQ ID NO: 13; and
    a light chain variable domain comprising the amino acid sequence of SEQ ID NO: 14,
    wherein said antibody, or antigen-binding portion thereof, binds to Globo H.

8. An antibody, or an antigen-binding portion thereof, comprising:
    a heavy chain variable domain comprising the amino acid sequence of SEQ ID NO:21; and
    a light chain variable domain comprising the amino acid sequence of SEQ ID NO:22,
    wherein the antibody, or antigen-binding portion thereof binds to Globo H.

9. An antibody, or an antigen-binding portion thereof, comprising:
    a heavy chain variable domain comprising the amino acid sequence of SEQ ID NO:29; and
    a light chain variable domain comprising the amino acid sequence of SEQ ID NO:30,
    wherein the antibody, or antigen-binding portion thereof, binds to Globo H.

10. An antibody, or an antigen-binding portion thereof, comprising:
    a heavy chain variable domain comprising the amino acid sequence of SEQ ID NO:37; and
    a light chain variable domain comprising the amino acid sequence of SEQ ID NO:38,
    wherein the antibody, or antigen-binding portion thereof, binds to Globo H.

11. An antibody, or an antigen-binding portion thereof, wherein the antibody is produced by a hybridoma selected from the group consisting of the hybridoma designated as 2C2 deposited under ATCC Number PTA-121138, the hybridoma designated as 3D7 deposited under ATCC Number PT A-121310, the hybridoma designated as 7A11 deposited under ATCC Number PTA-121311, the hybridoma designated as 2F8 deposited under ATCC Number PTA-121137 and the hybridoma designated as 1E1 deposited under ATCC Number PTA-121312, and
    wherein the antibody, or antigen-binding portion thereof, binds to Globo H.

* * * * *